United States Patent
Feldstein et al.

(10) Patent No.: US 8,821,901 B2
(45) Date of Patent: Sep. 2, 2014

(54) METHOD OF PREPARING POLYMERIC ADHESIVE COMPOSITIONS UTILIZING THE MECHANISM OF INTERACTION BETWEEN THE POLYMER COMPONENTS

(75) Inventors: Mikhail M. Feldstein, Moscow (RU); Danir F. Bairamov, Moscow (RU); Nicolai A. Platé, Moscow (RU); Valery G. Kulichikhin, Moscow (RU); Anatoly E. Chalykh, Moscow (RU); Gary W. Cleary, Los Altos Hills, CA (US); Parminder Singh, San Francisco, CA (US)

(73) Assignees: A.V. Topchiev Institute of Petrochemical Synthesis Russian Academy of Sciences, Moscow (RU); Corium International, Inc., Menlo Park, CA (US)

( * ) Notice: Subject to any disclaimer, the term of this patent is extended or adjusted under 35 U.S.C. 154(b) by 7 days.

(21) Appl. No.: 12/754,331

(22) Filed: Apr. 5, 2010

(65) Prior Publication Data
US 2010/0239644 A1    Sep. 23, 2010

Related U.S. Application Data

(62) Division of application No. 10/936,887, filed on Sep. 8, 2004, now abandoned.

(51) Int. Cl.
| | |
|---|---|
| *A61K 8/02* | (2006.01) |
| *A61K 8/18* | (2006.01) |
| *A61Q 11/00* | (2006.01) |
| *A01N 39/00* | (2006.01) |
| *A61K 33/40* | (2006.01) |
| *A61K 6/00* | (2006.01) |

(52) U.S. Cl.
CPC ............... *A61Q 11/00* (2013.01); *A61K 6/0067* (2013.01)
USPC ............................. 424/401; 424/49; 424/616

(58) Field of Classification Search
CPC ............................. A61Q 11/00; A61K 6/0067
USPC ............................................ 424/49, 401, 616
See application file for complete search history.

(56) References Cited

U.S. PATENT DOCUMENTS

| 2,561,071 A | 7/1951 | Prisk |
| 2,579,403 A | 12/1951 | Slomowitz et al. |

(Continued)

FOREIGN PATENT DOCUMENTS

| CA | 2520986 | 4/2000 |
| CA | 2402021 | 9/2001 |
| CA | 2451431 | 1/2003 |

(Continued)

OTHER PUBLICATIONS

Barbucci et al. "Swelling behavior of carboxymethylcellulose hydrogels in relation to cross-linking, pH, and charge density", Macromolecules, vol. 33, No. 20, pp. 7475-7480 (2000).

(Continued)

*Primary Examiner* — Benjamin Packard
(74) *Attorney, Agent, or Firm* — Susan T. Evans; McDermott Will & Emery LLP

(57) ABSTRACT

A method of selecting components for use in water-absorbing pressure-sensitive adhesive compositions is provided. The method involves selecting a film-forming polymer, a ladder-like non-covalent crosslinker that is capable of forming a ladder-like interpolymer complex with the film-forming polymer selected, and selecting a carcass-like non-covalent crosslinker that is capable of forming a carcass-like complex with at least one of the film-forming polymer selected or the ladder-like non-covalent crosslinker selected. The adhesive hydrogels provide high adhesion in a swollen state and bridge the gap between conventional pressure sensitive adhesives and bioadhesives. Methods for preparing and using the resulting compositions are also disclosed.

21 Claims, 6 Drawing Sheets

(56) References Cited

U.S. PATENT DOCUMENTS

| | | |
|---|---|---|
| 3,150,977 A | 9/1964 | Hart et al. |
| 3,689,439 A | 9/1972 | Field et al. |
| 3,721,657 A | 3/1973 | Seiderman |
| 3,749,755 A | 7/1973 | Bronstart et al. |
| 3,852,228 A | 12/1974 | Brothers |
| 3,957,605 A | 5/1976 | Assarsson et al. |
| 3,993,551 A | 11/1976 | Assarsson et al. |
| 3,996,934 A | 12/1976 | Zaffaroni |
| 4,091,090 A | 5/1978 | Sipos |
| 4,093,673 A | 6/1978 | Chang et al. |
| 4,160,020 A | 7/1979 | Ayer et al. |
| 4,231,369 A | 11/1980 | Sorensen et al. |
| 4,277,580 A | 7/1981 | Allen et al. |
| 4,325,851 A | 4/1982 | Colon et al. |
| 4,346,709 A | 8/1982 | Schmitt et al. |
| 4,367,732 A | 1/1983 | Poulsen et al. |
| 4,492,685 A | 1/1985 | Keith et al. |
| 4,529,601 A | 7/1985 | Broberg et al. |
| 4,552,751 A | 11/1985 | Inaba et al. |
| 4,557,934 A | 12/1985 | Cooper |
| 4,562,060 A | 12/1985 | Broberg et al. |
| 4,568,343 A | 2/1986 | Leeper et al. |
| 4,587,289 A | 5/1986 | Comert et al. |
| 4,593,053 A | 6/1986 | Jevne et al. |
| 4,624,665 A | 11/1986 | Nuwayser |
| 4,699,146 A | 10/1987 | Sieverding |
| 4,713,243 A | 12/1987 | Schiraldi et al. |
| 4,743,249 A | 5/1988 | Loveland |
| 4,750,482 A | 6/1988 | Sieverding |
| 4,771,105 A | 9/1988 | Shirai et al. |
| 4,849,224 A | 7/1989 | Chang et al. |
| 4,863,738 A | 9/1989 | Taskovich |
| 4,863,970 A | 9/1989 | Patel et al. |
| 4,867,748 A | 9/1989 | Samuelsen |
| 4,871,536 A | 10/1989 | Arraudeau et al. |
| 4,873,299 A | 10/1989 | Nawoakowsky et al. |
| 4,877,628 A | 10/1989 | Stypula |
| 4,904,247 A | 2/1990 | Therriault et al. |
| 4,906,169 A | 3/1990 | Chien et al. |
| 4,927,408 A | 5/1990 | Haak et al. |
| 4,945,084 A | 7/1990 | Packman |
| 4,953,053 A | 8/1990 | Pratt |
| 4,973,468 A | 11/1990 | Chiang et al. |
| 4,983,395 A | 1/1991 | Chang et al. |
| 5,023,084 A | 6/1991 | Chien et al. |
| 5,053,227 A | 10/1991 | Chiang et al. |
| 5,057,500 A | 10/1991 | Thornfeldt |
| 5,073,381 A | 12/1991 | Ivan et al. |
| 5,102,662 A | 4/1992 | Gallagher |
| 5,125,894 A | 6/1992 | Phipps et al. |
| 5,133,970 A | 7/1992 | Petereit et al. |
| 5,141,750 A | 8/1992 | Lee et al. |
| 5,173,302 A | 12/1992 | Holmblad et al. |
| 5,183,901 A | 2/1993 | Login et al. |
| 5,196,405 A | 3/1993 | Packman |
| 5,200,190 A | 4/1993 | Azuma et al. |
| 5,206,385 A | 4/1993 | Login et al. |
| 5,224,928 A | 7/1993 | Sibalis et al. |
| 5,232,702 A | 8/1993 | Pfister et al. |
| 5,234,690 A | 8/1993 | Chiang et al. |
| 5,234,957 A | 8/1993 | Mantelle |
| 5,240,995 A | 8/1993 | Gyory et al. |
| 5,254,346 A | 10/1993 | Tucker et al. |
| 5,270,358 A | 12/1993 | Asmus |
| 5,276,079 A | 1/1994 | Duan et al. |
| 5,296,512 A | 3/1994 | Beier et al. |
| 5,300,291 A | 4/1994 | Sablotsky et al. |
| 5,310,563 A | 5/1994 | Curtis et al. |
| 5,322,689 A | 6/1994 | Hughes et al. |
| 5,326,685 A | 7/1994 | Gaglio et al. |
| 5,332,576 A | 7/1994 | Mantelle |
| 5,338,490 A | 8/1994 | Dietz et al. |
| 5,342,623 A | 8/1994 | Enscore et al. |
| 5,344,394 A | 9/1994 | Gyory et al. |
| 5,354,823 A | 10/1994 | Tseng et al. |
| 5,362,420 A | 11/1994 | Itoh et al. |
| 5,376,377 A | 12/1994 | Gale et al. |
| 5,422,119 A | 6/1995 | Casper |
| 5,438,076 A | 8/1995 | Friedman et al. |
| 5,446,070 A | 8/1995 | Mantelle |
| 5,456,745 A | 10/1995 | Roreger et al. |
| 5,462,743 A | 10/1995 | Turner et al. |
| 5,462,745 A | 10/1995 | Enscore et al. |
| 5,492,943 A | 2/1996 | Stempel |
| 5,508,024 A | 4/1996 | Tranner |
| 5,508,367 A | 4/1996 | Zajaczkowski |
| 5,527,271 A | 6/1996 | Shah et al. |
| 5,543,148 A | 8/1996 | Lapidus |
| 5,563,153 A | 10/1996 | Mueller et al. |
| 5,575,654 A | 11/1996 | Fontenot |
| 5,593,686 A | 1/1997 | Kissel et al. |
| 5,594,068 A | 1/1997 | Buchanan et al. |
| 5,599,373 A | 2/1997 | Zanuccoli |
| 5,614,178 A | 3/1997 | Bloom et al. |
| 5,631,267 A | 5/1997 | Gleich et al. |
| 5,633,010 A | 5/1997 | Chen |
| 5,641,504 A | 6/1997 | Lee et al. |
| 5,641,507 A | 6/1997 | DeVillez |
| 5,643,187 A | 7/1997 | Naestoft et al. |
| 5,645,062 A | 7/1997 | Anderson et al. |
| 5,645,855 A | 7/1997 | Lorenz |
| 5,656,286 A | 8/1997 | Miranda et al. |
| 5,660,178 A | 8/1997 | Kantner et al. |
| 5,662,925 A | 9/1997 | Ebert et al. |
| 5,663,010 A | 9/1997 | Stocchiero |
| 5,674,561 A | 10/1997 | Dietz et al. |
| 5,700,478 A | 12/1997 | Biegajski et al. |
| 5,702,721 A | 12/1997 | Horstmann et al. |
| 5,718,187 A | 2/1998 | Pollock et al. |
| 5,718,886 A | 2/1998 | Pellico |
| 5,719,197 A | 2/1998 | Kanios et al. |
| 5,723,145 A | 3/1998 | Shikinami et al. |
| 5,725,876 A | 3/1998 | Mantelle et al. |
| 5,726,250 A | 3/1998 | Zajaczkowski |
| 5,730,999 A | 3/1998 | Lehmann et al. |
| 5,744,155 A | 4/1998 | Friedman et al. |
| 5,762,956 A | 6/1998 | Chien |
| 5,770,220 A | 6/1998 | Meconi et al. |
| 5,773,490 A | 6/1998 | Shikinami et al. |
| 5,780,050 A | 7/1998 | Jain et al. |
| 5,785,527 A | 7/1998 | Jensen et al. |
| 5,785,976 A | 7/1998 | Westesen et al. |
| 5,788,983 A | 8/1998 | Chien et al. |
| 5,800,832 A | 9/1998 | Tapolsky et al. |
| 5,804,611 A | 9/1998 | Takoh et al. |
| 5,827,213 A | 10/1998 | Jensen |
| 5,827,525 A | 10/1998 | Liao et al. |
| 5,830,932 A | 11/1998 | Kay |
| 5,837,713 A | 11/1998 | Gleich et al. |
| 5,843,472 A | 12/1998 | Ma et al. |
| 5,846,558 A | 12/1998 | Nielsen et al. |
| 5,851,549 A | 12/1998 | Svec |
| 5,853,755 A | 12/1998 | Foldvari |
| 5,858,332 A | 1/1999 | Jensen et al. |
| 5,858,410 A | 1/1999 | Muller et al. |
| 5,863,662 A | 1/1999 | Hornby et al. |
| 5,876,746 A | 3/1999 | Jona et al. |
| 5,879,691 A | 3/1999 | Sagel et al. |
| 5,879,701 A | 3/1999 | Audett et al. |
| 5,891,453 A | 4/1999 | Sagel et al. |
| 5,894,017 A | 4/1999 | Sagel et al. |
| 5,900,249 A | 5/1999 | Smith |
| 5,902,598 A | 5/1999 | Chen et al. |
| 5,911,980 A | 6/1999 | Samour et al. |
| 5,912,271 A | 6/1999 | Brodine et al. |
| 5,916,587 A | 6/1999 | Min et al. |
| 5,942,543 A | 8/1999 | Ernst |
| 5,945,032 A | 8/1999 | Breitenbach et al. |
| 5,945,457 A | 8/1999 | Plate et al. |
| 5,948,416 A | 9/1999 | Wagner et al. |
| 5,948,430 A | 9/1999 | Zerbe et al. |
| 5,948,433 A | 9/1999 | Burton et al. |
| 5,958,379 A | 9/1999 | Regenold et al. |
| 5,958,446 A | 9/1999 | Miranda et al. |

(56) References Cited

U.S. PATENT DOCUMENTS

| | | |
|---|---|---|
| 5,962,011 A | 10/1999 | DeVillez |
| 5,972,377 A | 10/1999 | Jona et al. |
| 5,976,565 A | 11/1999 | Fotinos |
| 5,985,311 A | 11/1999 | Cordes et al. |
| 5,985,860 A | 11/1999 | Toppo |
| 5,985,990 A | 11/1999 | Kantner et al. |
| 5,989,569 A | 11/1999 | Dirksing et al. |
| 5,990,179 A | 11/1999 | Gyori et al. |
| 5,993,836 A | 11/1999 | Castillo |
| 5,993,849 A | 11/1999 | Assmus et al. |
| 5,997,886 A | 12/1999 | Peffly et al. |
| 6,004,566 A | 12/1999 | Freidman et al. |
| 6,004,578 A | 12/1999 | Lee et al. |
| 6,007,837 A | 12/1999 | Enscore et al. |
| 6,024,976 A | 2/2000 | Miranda et al. |
| 6,045,811 A | 4/2000 | Dirksing et al. |
| 6,051,609 A | 4/2000 | Yu et al. |
| 6,063,399 A | 5/2000 | Assmus et al. |
| 6,068,650 A | 5/2000 | Hofmann et al. |
| 6,072,100 A | 6/2000 | Mooney et al. |
| 6,075,626 A | 6/2000 | Mizutani et al. |
| 6,083,421 A | 7/2000 | Huang et al. |
| 6,093,328 A | 7/2000 | Santina |
| 6,096,328 A | 8/2000 | Sagel et al. |
| 6,135,126 A | 10/2000 | Joshi |
| 6,142,939 A | 11/2000 | Eppstein et al. |
| 6,146,654 A | 11/2000 | Kubo |
| 6,153,215 A | 11/2000 | Samuelsen et al. |
| 6,162,456 A | 12/2000 | Dunbar et al. |
| 6,165,499 A | 12/2000 | Kleinsorgen et al. |
| 6,177,096 B1 | 1/2001 | Zerbe et al. |
| 6,193,993 B1 | 2/2001 | Murahashi et al. |
| 6,197,331 B1 | 3/2001 | Lerner et al. |
| 6,201,164 B1 | 3/2001 | Wulff et al. |
| 6,212,671 B1 | 4/2001 | Kanehira et al. |
| 6,221,341 B1 | 4/2001 | Montgomery |
| 6,221,383 B1 | 4/2001 | Miranda et al. |
| 6,231,885 B1 | 5/2001 | Carrara |
| 6,248,363 B1 | 6/2001 | Patel et al. |
| 6,264,981 B1 | 7/2001 | Zhang et al. |
| 6,270,792 B1 | 8/2001 | Guillemet et al. |
| 6,275,728 B1 | 8/2001 | Venkatraman et al. |
| 6,306,370 B1 | 10/2001 | Jensen et al. |
| 6,312,666 B1 | 11/2001 | Oxman et al. |
| 6,312,670 B1 | 11/2001 | Montgomery |
| 6,316,022 B1 | 11/2001 | Mantelle et al. |
| 6,322,774 B1 | 11/2001 | Jensen et al. |
| 6,329,472 B1 | 12/2001 | Kim et al. |
| 6,368,576 B1 | 4/2002 | Jensen et al. |
| 6,419,905 B1 | 7/2002 | Alvarez Hernandez |
| 6,419,906 B1 | 7/2002 | Xu et al. |
| 6,451,240 B1 | 9/2002 | Sherman et al. |
| 6,451,777 B1 | 9/2002 | Bradbury et al. |
| 6,461,636 B1 | 10/2002 | Arth et al. |
| 6,488,913 B2 | 12/2002 | Orlowski et al. |
| 6,517,350 B2 | 2/2003 | Diasti et al. |
| 6,552,147 B2 | 4/2003 | Parker et al. |
| 6,558,654 B2 | 5/2003 | McLaughlin |
| 6,562,363 B1 | 5/2003 | Mantelle et al. |
| 6,576,712 B2 | 6/2003 | Feldstein et al. |
| 6,585,997 B2 | 7/2003 | Moro et al. |
| 6,591,124 B2 | 7/2003 | Sherman et al. |
| 6,596,298 B2 | 7/2003 | Leung et al. |
| 6,602,912 B2 | 8/2003 | Hsu et al. |
| 6,611,706 B2 | 8/2003 | Avrahami et al. |
| 6,638,528 B1 | 10/2003 | Kanios |
| 6,656,493 B2 | 12/2003 | Dzija |
| 6,667,410 B2 | 12/2003 | Manbus et al. |
| 6,673,363 B2 | 1/2004 | Luo et al. |
| 6,682,721 B2 | 1/2004 | Kim et al. |
| 6,689,344 B2 | 2/2004 | Chang et al. |
| 6,696,459 B1 | 2/2004 | Jones et al. |
| 6,708,060 B1 | 3/2004 | Avrahami et al. |
| 6,709,671 B2 | 3/2004 | Zerbe et al. |
| 6,711,435 B2 | 3/2004 | Avrahami |
| 6,714,497 B2 | 3/2004 | Cleary et al. |
| 6,750,291 B2 | 6/2004 | Kim et al. |
| 6,759,030 B2 | 7/2004 | Kosti |
| 6,762,202 B2 | 7/2004 | Marek et al. |
| 6,780,401 B2 | 8/2004 | Kim et al. |
| 6,783,769 B1 | 8/2004 | Arth et al. |
| 6,803,420 B2 | 10/2004 | Cleary et al. |
| 6,805,874 B1 | 10/2004 | Lutz et al. |
| 6,806,308 B2 | 10/2004 | Zajac |
| 6,884,833 B2 | 4/2005 | Cheang et al. |
| 6,946,142 B2 | 9/2005 | Chang et al. |
| 6,962,691 B1 | 11/2005 | Lulla et al. |
| 7,078,359 B2 | 7/2006 | Stepanian et al. |
| 7,112,713 B2 | 9/2006 | Sceusa |
| 7,122,199 B2 | 10/2006 | Sagel et al. |
| 7,138,458 B2 | 11/2006 | Cleary et al. |
| 7,217,853 B2 | 5/2007 | Kulichikhin et al. |
| 7,323,161 B2 | 1/2008 | Choi et al. |
| 7,384,650 B2 | 6/2008 | Chien |
| 7,456,331 B2 | 11/2008 | Kulichikhin et al. |
| 7,744,918 B2 | 6/2010 | Yamaguchi et al. |
| 2001/0006677 A1 | 7/2001 | Mcginity et al. |
| 2001/0021374 A1 | 9/2001 | Montgomery |
| 2001/0046471 A1 | 11/2001 | Marek et al. |
| 2002/0004190 A1 | 1/2002 | Diasti et al. |
| 2002/0009420 A1 | 1/2002 | McLaughlin |
| 2002/0048602 A1 | 4/2002 | Flore et al. |
| 2002/0076487 A1 | 6/2002 | Zajac |
| 2002/0106335 A1 | 8/2002 | Orlowski et al. |
| 2002/0131990 A1 | 9/2002 | Barkalow et al. |
| 2002/0197284 A1 | 12/2002 | Luo et al. |
| 2003/0035841 A1 | 2/2003 | Dzija |
| 2003/0055190 A1 | 3/2003 | Parker et al. |
| 2003/0068376 A1 | 4/2003 | Chen et al. |
| 2003/0100654 A1 | 5/2003 | Cheang et al. |
| 2003/0103427 A1 | 6/2003 | Cleary et al. |
| 2003/0152528 A1* | 8/2003 | Singh et al. .................. 424/53 |
| 2003/0152615 A1 | 8/2003 | Houze et al. |
| 2003/0170308 A1 | 9/2003 | Cleary et al. |
| 2003/0180229 A1 | 9/2003 | Kosti |
| 2003/0225356 A1 | 12/2003 | Kulichikhin et al. |
| 2003/0235549 A1* | 12/2003 | Singh et al. .............. 424/70.13 |
| 2004/0005277 A1 | 1/2004 | Willison et al. |
| 2004/0053901 A1 | 3/2004 | Chien |
| 2004/0105834 A1 | 6/2004 | Singh et al. |
| 2004/0136927 A1 | 7/2004 | Kim et al. |
| 2004/0166147 A1 | 8/2004 | Lundy et al. |
| 2004/0219111 A1 | 11/2004 | Kim et al. |
| 2004/0258723 A1 | 12/2004 | Singh et al. |
| 2005/0031554 A1 | 2/2005 | Kim et al. |
| 2005/0113510 A1 | 5/2005 | Feldstein et al. |
| 2005/0208110 A1 | 9/2005 | Singh et al. |
| 2005/0215727 A1 | 9/2005 | Feldstein et al. |
| 2005/0228113 A1 | 10/2005 | Baumer et al. |
| 2005/0256223 A1 | 11/2005 | Kolb et al. |
| 2006/0034905 A1 | 2/2006 | Singh et al. |
| 2006/0110434 A1 | 5/2006 | Yamaguchi et al. |
| 2006/0168905 A1 | 8/2006 | Blanc et al. |
| 2006/0171906 A1 | 8/2006 | Singh et al. |
| 2006/0182788 A1 | 8/2006 | Singh et al. |
| 2006/0193793 A1 | 8/2006 | Kim et al. |
| 2006/0193794 A1 | 8/2006 | Kim et al. |
| 2008/0161492 A1 | 7/2008 | Cleary et al. |
| 2009/0258060 A1 | 10/2009 | Cleary et al. |

FOREIGN PATENT DOCUMENTS

| | | |
|---|---|---|
| CA | 2506073 | 6/2004 |
| DE | 8509793 | 5/1985 |
| DE | 4219368 | 6/1992 |
| EP | 0184470 | 6/1986 |
| EP | 0303445 | 2/1989 |
| EP | 0364211 | 4/1990 |
| EP | 0371421 | 6/1990 |
| EP | 0511782 | 11/1992 |
| EP | 0516026 | 12/1992 |
| EP | 0545594 | 6/1993 |
| EP | 0581581 | 2/1994 |
| EP | 0672094 | 9/1995 |

(56) References Cited

FOREIGN PATENT DOCUMENTS

| | | |
|---|---|---|
| EP | 0737477 | 10/1996 |
| EP | 0838225 | 4/1998 |
| EP | 0848960 | 6/1998 |
| EP | 1066823 | 1/2001 |
| GB | 1108837 | 4/1968 |
| JP | 58-162681 | 9/1983 |
| JP | 59-196817 | 11/1984 |
| JP | 01-151524 | 6/1989 |
| JP | 03-066612 | 3/1991 |
| JP | 03-247334 | 5/1991 |
| JP | 03-275619 | 6/1991 |
| JP | 04-266818 | 9/1992 |
| JP | 06-100467 | 4/1994 |
| JP | 10-017448 | 1/1998 |
| JP | 2001-213768 | 7/2001 |
| JP | 2002-029949 | 1/2002 |
| JP | 2002-145746 | 5/2002 |
| KR | 20020045224 | 6/2002 |
| KR | 20030000299 | 1/2003 |
| KR | 20030000528 | 1/2003 |
| KR | 20030003969 | 1/2003 |
| KR | 20030003973 | 1/2003 |
| RU | 1459215 | 11/1995 |
| WO | WO 89/03859 | 5/1989 |
| WO | WO 90/07940 A1 | 7/1990 |
| WO | WO 93/02717 | 2/1993 |
| WO | WO 94/05340 | 3/1994 |
| WO | WO 96/19205 | 6/1996 |
| WO | WO 97/11676 | 4/1997 |
| WO | WO 98/20862 A1 | 5/1998 |
| WO | WO 98/26763 | 6/1998 |
| WO | WO 98/37870 | 9/1998 |
| WO | WO 98/55044 | 12/1998 |
| WO | WO 99/11728 A1 | 3/1999 |
| WO | WO 99/17738 | 4/1999 |
| WO | WO 99/44678 | 9/1999 |
| WO | WO 99/47128 | 9/1999 |
| WO | WO 99/54422 | 10/1999 |
| WO | WO 99/55312 A2 | 11/1999 |
| WO | WO 00/16725 | 3/2000 |
| WO | WO 00/18365 A2 | 4/2000 |
| WO | WO 00/61120 A1 | 10/2000 |
| WO | WO 00/69421 | 11/2000 |
| WO | WO 01/01958 A1 | 1/2001 |
| WO | WO 01/07018 A1 | 2/2001 |
| WO | WO 01/26637 | 4/2001 |
| WO | WO 01/68045 | 9/2001 |
| WO | WO 01/87276 | 11/2001 |
| WO | WO 02/00182 A3 | 1/2002 |
| WO | WO 02/04570 | 1/2002 |
| WO | WO 02/087642 | 11/2002 |
| WO | WO 02/087645 | 11/2002 |
| WO | WO 02/089849 | 11/2002 |
| WO | WO 03/000216 | 1/2003 |
| WO | WO 03/089046 | 10/2003 |
| WO | WO 03/099344 | 12/2003 |
| WO | WO 2004/045569 | 6/2004 |
| WO | WO 2004/054638 | 7/2004 |
| WO | WO 2004/071323 | 8/2004 |
| WO | WO 2004/093786 | 11/2004 |
| WO | WO 2004/103201 | 12/2004 |
| WO | WO 2005/027768 | 3/2005 |
| WO | WO 2006/017807 | 2/2006 |
| WO | WO 2006/029407 | 3/2006 |
| WO | WO 2006/069236 | 6/2006 |
| WO | WO 2006/074173 | 7/2006 |
| WO | WO 2006/081497 | 8/2006 |
| WO | WO 2006/124639 | 11/2006 |
| WO | WO 2007/119656 | 10/2007 |
| WO | WO 2010/083035 | 7/2010 |

OTHER PUBLICATIONS

Emla Cream, (lidocaine 2.5% and prilocaine 2.5%), EMLA Anesthetic Disc, (lidocaine 2.5% and prilocaine 2.5% cream), "Topical anesthetic for dermal analgesia", AstraZeneca Product Monograph, 46 pgs, Revised May 25, 2010.

EUDRAGIT® RL 100, "EUDRAGIT® RL 100 is a copolymer of ethyl acrylate, methyl methacrylate and a low content of methacrylic acid ester with quaternary ammonium groups. The ammonium groups are present as salts and make the polymers permeable", Product Information, Accessed online from: http://eudragit.evonik.com/product/eudragit/en/products-services/eudragit-products/sustained-release-formulations/rl-100/pages/default.aspx, 1 page, accessed on Apr. 15, 2011.

EUDRAGIT® RS 100, "EUDRAGIT® RS 100 is a copolymer of ethyl acrylate, methyl methacrylate and a low content of methacrylic acid ester with quaternary ammonium groups. The ammonium groups are present as salts and make the polymers permeable", Product information, Accessed online from: http://eudragit.evonik.com/product/eudragit/en/products-services/eudragit-products/sustained-release-formulations/rs-100/pages/default.aspx, 1 page, accessed on Apr. 15, 2011.

Evonic Industries, "EUDRAGIT® E 100: EUDRAGIT® E 100 is a cationic copolymer based on dimethylaminoethyl methacrylate, butyl methacrylate, and methyl methacrylate", Product Information, Accessed Online from http://eudragit.evonik.com, 1 page (2011).

Evonic Industries, "EUDRAGIT® L 12,5 and EUDRAGIT® S 12,5", Product Information, Accessed Online from http://eudragit.evonik.com, 1 page (2011).

Evonic Industries, "EUDRAGIT® RL 12,5 and EUDRAGIT® RS 12,5", Product Information, Accessed Online from http://eudragit.evonik.com, 1 page (2011).

Evonic Industries, "EUDRAGIT® NE 30 D: EUDRAGIT® NE 30 D is the aqueous dispersion of a neutral copolymer based on ethyl acrylate and methyl methacrylate", Product Information, Accessed Online from http://eudragit.evonik.com, 1 page (2011).

Feldstein et al., "A new class of pressure-sensitive adhesives based on interpolymer and polymer-oligomer complexes", Polymer Science, vol. 51, No. 7, pp. 799-814 (2009).

Whelan Polymer Technology Dictionary, Citation Butyl Rubber, Chapman Hall, 2-6 Boundry Row, London, UK, vol. 1, pp. 53 (1994).

U.S. Appl. No. 11/150,811, filed Jun. 10, 2005, Feldstein et al.

U.S. Appl. No. 12/687,586, filed Jan. 11, 2009, Singh et al.

Aubin et al., "Analysis of the glass transistion temperature of miscible polymer blends", Macromolecules, vol. 21, pp. 2945-2949, (1988).

Bairamov et al., "Kinetic parameters of poly(N-vinyl pyrrolidone) spontaneous mixing with short-chain poly(ethylene glycol)", Polym. Mater. Sci. Eng., vol. 82, pp. 7-8, (2000).

Borodulina et al. "Viscoelasticity of Pressure-sensitive adhesive and bioadhesive hydrogels under compressive load", Proceed. 24th Annual Meeting Adhesion Soc., pp. 147-149, (2001).

Chalykh et al., "Effects of composition and hydration on adhesive properties of poly(N-vinyl pyrrolidone)-poly(ethylene glycol) hydrogels", Polym. Mater. Sci. Eng., vol. 81, pp. 456-457, (1999).

Chalykh et al., "Fracture mechanics of poly(N-vinyl pyrrolidone)-poly(ethylene glycol) hydrogel adhesive joints," Polym. Mater. Sci. Eng., vol. 81, pp. 427-428, (1999).

Chalykh et al., "Pressure-sensitive adhesion in the blends of poly(N-vinyl pyrrolidone) and poly(ethylene glycol) of disparate chain lengths," J. Adhesion, vol. 78, pp. 667-694, (2002).

Cleary et. al., A new polymer blend adhesive with combined properties to adhere to either skin or mucosa for drug delivery, podium abstract, 30th Annual Meeting and Exposition of the Controlled Release Society, Glasgow, Scotland, Jul. 19-23, 2003, Abstract #123.

Database WPI Section Ch, Week 198451, Derwent Publictions Ltd., London, GB; AN 1984-315114 & JP 59196817 A (Sekisuki Chem Ind Co Ltd) Nov. 8, 1984 abstract.

Database WPI Section Ch, Week 199150, Derwent Publications Ltd., London, GB; AN 1991-366353 & JP 03247334 A (Sumitomo Rubber Ind Ltd) Nov. 5, 1991 abstract.

Database WPI Section Ch, Week 199118, Derwent Publications Ltd., London, GB; AN 1991-128478 & JP 03066612 A (Sato Pharm Co Ltd) Mar. 22, 1991 abstract.

(56) References Cited

OTHER PUBLICATIONS

Emla Cream, (lidocaine 2.5% and prilocaine 2.5%), EMLA Anesthetic Disc, (lidocaine 2.5% and prilocaine 2.5% cream), Topical adhesive system, Detailed description.
Feldstein et al., "Effect of hydrophilic matrix hydration on transdermal drug delivery kinetics: IV. In Vitro-In Vivo correlation," Prediction of Percutaneous Penetration, vol. 4b, pp. 71-73, Brian, et al., (eds.) (1996).
Feldstein et al., "Effects of chains orientation, free volume and interaction on glass transition in poly(N-vinyl pyrrolidone)-poly(ethylene glycol) blends involving a stoichiometric hydrogen-Bbonded network complex", Polym. Mater. Sci. Eng., vol. 82, pp. 365-366, (2000).
Feldstein et al., "General approach to the molecular design of hydrophilic pressure-sensitive adhesives," Proc. 25th Ann. Mtg. and 2nd World Congress on Adhesion and Related Phenomena, Orlando, FL, vol. 1, pp. 292-294 (2002).
Feldstein et al., "Molecular insight into rheologival and diffusion determinants of pressure sensitive adhesion", Proceed. 23rd Annual Meeting Adhesion Soc., pp. 54-56, (2000).
Feldstein et al., "Peculiarities of glass transition temperature relation to the composition of poly(N-vinyl pyrrolidone) blends with short chain poly(ethylene glycol)", Polymer, vol. 42, pp. 7719-7726, (2001).
Feldstein et al., "Quantitative relationship between molecular structure and adhesion of PVP-PEG hydrogels", Polym. Mater. Sci Eng., vol. 81, pp. 465-466, (1999).
Feldstein et al., "Relation of glass transition temperature to the hydrogen bonding degree and energy in poly(N-vinyl pyrrolidone) blends with hydroxyl-containing plasticizers: 2. Effects of poly(ethylene glycol) chain length", Polymer, vol. 42, pp. 981-990, (2001).
Feldstein et al., "Universal hydrophilic drug-containing adhesive matrix for systemic and topical transdermal drug delivery", Proc. 1st World Meeting APGI/APV, Budapest, Sep. 2011, 2 pages, (1995).
Handbook of Pharmaceutical Excipients, Arther H. Kibbe, ed., 3rd ed., pp. 401-406, (2000).
Hawley's Condensed Chemical Dictionary, 14th Edition, Citation, "Oligomer, A polymer molecule of only a few monomer units (dimer, trimer, tetramer)", John Wiley and Sons, Inc., (2002).
International Search Report for PCT/US2000/18557 mailed Oct. 17, 2000.
International Search Report for PCT/US2001/21417 mailed Feb. 25, 2002.
International Search Report for PCT/US2002/13680 mailed Sep. 18, 2002.
International Search Report for PCT/US2002/14260 Mailed Sep. 17, 2002.
International Search Report for PCT/US2002/14725 mailed Sep. 27, 2002.
International Search Report for PCT/US2003/16408 Mailed Dec. 8, 2003.
International Search Report for PCT/US2003/039717 Mailed Jun. 28, 2004.
International Search Report for PCT/US2004/003443 Mailed Aug. 20, 2004.
International Search Report for PCT/US2004/011567 Mailed Jan. 10, 2006.
International Search Report for PCT/US2004/015448 Mailed Dec. 28, 2004.
International Search Report for PCT/US2004/029620 Mailed Jun. 1, 2005.
International Search Report for PCT/US2005/0002873 Mailed Apr. 27, 2005.
International Search Report for PCT/US2005/0034439 Mailed Jul. 19, 2006.
International Search Report for PCT/US2005/0046577 Mailed Jul. 26, 2006.
International Search Report for PCT/US/2005/028063 Mailed Apr. 28, 2006.
International Search Report for PCT/US/2005/032525 Mailed Mar. 17, 2006.
International Search Report for PCT/US/2006/000098 Mailed Nov. 3, 2006.
International Search Report for PCT/US2006/0003091 Mailed Oct. 11, 2006.
International Search Report for PCT/US2006/018500 Mailed Sep. 21, 2006.
Kotomin et al., "Squeeze-recoil analysis of adhesive hydrogels and elastomers", Polym. Mater. Sci. Eng., vol. 81, pp. 425-426, (1999).
Kotomin et al., "Durability and fracture of some visceolastic adhesives," Proceed. Of the 23rd Annual Meeting of the Adhesion Soc., pp. 413-415, (2000).
MSDS (Material Safety Data Sheet), Lactic Acid, No. L0522, (2008).
Patent Abstracts of Japan, vol. 017, No. 055 (C-I023) Feb. 3, 1993 & JP 04 266818 A (Sekisui Chem Co Ltd), Sep. 22, 1992 abstract.
Roos et al., "Probe tack investigation of poly(vinyl pyrrolidone)-poly(ethylene glycol) blends", Proceed. 24th Annual Meeting Adhesion Soc., pp. 277-279, (2001).
Schehlmann "Polyvinylcaprolactam: physical and cosmetic properties of a new hari fixative resin", Lecture, SOFW-Journal-Sounderdruck, 6 pages (1997).
Sintov et al., "Radiofrequency-driven skin microchanneling as a new way for electically assisted transdermal delivery of hydrophilic drugs", J. Contr.Release, vol. 89, pp. 311-320, (2003).
Supplementary European Search Report for EP04783729.9 Mailed Jun. 5, 2009.
Vartapian et al., "Self-diffusion in poly(N-vinyl pyrrolidone)-poly-(ethylene glycol) systems", Colloid Polym. Sci., vol. 279, pp. 532-538, (2001).
Vartapian et al., "Molecular dynamics in poly(N-vinyl pyrrolidone)-poly(ethylene glycol) blends by pulsed-field gradient NMR method: effects of aging, hydration and PEG chain length", Macromol. Chem. Phys., vol. 202, pp. 2648-2652, (2001).
Database WPI Section Ch, Week 199627, Derwent Publications Ltd., London, GB; AN 1996-266746 & SU 1459215 A (A Med Cardiology Res Centre) Nov. 20, 1995 abstract.
Feldstein et al., "A structure—property relationship and quantitative approach to the development of universal transdermal drug delivery system," NBC Risks, vol. 25, pp. 441-458, (1999).
Feldstein et al., "Coherence of thermal transitions in poly(N-vinyl pyrrolidone)-poly(ethylene glycol) compatible blends: 1. Interrelations among the temperatures of melting, maximum cold crystalization rate and glass transition", Polymer, vol. 41, pp. 5327-5338, (2000).
Feldstein et al., "Coherence of thermal transitions in poly(N-vinyl pyrrolidone)-poly(ethylene glycol) compatible blends: 2. The temperature of maximum cold crystalization rate versus glass transition", Polymer, vol. 41, pp. 5339-5348, (2000).
Feldstein et al., "Coherence of thermal transitions in poly(N-vinyl pyrrolidone)-poly(ethylene glycol) compatible blends: 3. Impact of sorbed water upon phase behavior", Polymer, vol. 41, pp. 5439-5359, (2000).
Feldstein et al., "Correlations between activation energy for debonding and that for self-diffusion in pressure-sensitive hydrogels", Proceed. 24th Annual Meeting Adhession Soc., pp. 137-140, (2001).
Feldstein et al., "Contribution of molecular mobility to debonding of pressure-sensitive adhesive hydrogels", Polym. Mater. Sci. Eng., vol. 81, pp. 467-468, (1999).
Feldstein et al., "Effect of hydrophilic matrix hydration on transdermal drug delivery kinetics: I. The matrix hydration In Vivo and In Vitro", Prediction of Percutaneous Penetration, vol. 4b, pp. 61-64, Brian, et al., (Eds.) (1996).
Feldstein et al., "Effect of hydrophilic matrix hydration on transdermal drug delivery kinetics: II. In Vitro cytasine Delivery From Cypercuten TTS", Prediction of Percutaneous Penetration, vol. 4b, pp. 65-67, Brian, et al., (Eds.) (1996).
Feldstein et al., "Effect of hydrophilic matrix hydration on transdermal drug delivery kinetics: III. In Vitro clonide delivery from clopercuten TTS", Prediction of Percutaneous Penetration, vol. 4b, pp. 68-70, Brian, et al., (Eds.) (1996).

* cited by examiner

METHOD OF PREPARING POLYMERIC ADHESIVE COMPOSITIONS UTILIZING THE MECHANISM OF INTERACTION BETWEEN THE POLYMER COMPONENTS

CROSS-REFERENCE TO RELATED APPLICATIONS

This application is a divisional application of U.S. patent application Ser. No. 10/936,887, filed Sep. 8, 2004, now abandoned.

TECHNICAL FIELD

This invention relates to polymer compositions. More particularly, the invention relates to hydrogel and bioadhesive compositions, methods of selecting materials for manufacturing the compositions, and methods of using these compositions in therapeutic applications such as drug delivery systems (e.g., topical, transdermal, transmucosal, iontophoretic), medical skin coverings, wound dressings and wound healing products, and biomedical electrodes, as well as in cosmeceutical applications such as tooth whitening products.

BACKGROUND

Various types of bandages and wound dressings are known and used to protect wounds and burns. Typically, wound dressings are fabricated with an absorbent material so that wound exudate is removed and the wound dried, facilitating healing. Wound dressings may also contain one or more pharmacologically active agents such as antibiotics, local anesthetics, or the like. Commonly used wound dressings include fibrous materials such as gauze and cotton pads, which are advantageous in that they are absorbent but problematic in that fibers may adhere to the wound or newly forming tissue, causing wound injury upon removal. Other wound dressings have been prepared with foams and sponges, but the absorbance of these materials is often limited. Furthermore, such wound dressings require the use of adhesive tape, as they are not themselves adhesive.

Hydrophilic pressure-sensitive adhesives ("PSAs") are used in a variety of pharmaceutical and cosmetic products, such as topical and transdermal drug delivery systems, wound dressings, face masks, bioadhesive films designed for buccal and mucosal administration, teeth whitening strips, and so on. A general distinctive feature of hydrophilic PSAs is that they typically adhere to wet biological substrates, while conventional hydrophobic (rubber-based) PSAs typically lose their adhesive properties when moistened.

The adhesive properties of PSAs will vary depending upon how and where the products are to be used. For transdermal drug delivery and topical applications, an adhesive patch, for instance, should provide high tack immediately upon use, and such tack should be maintained during the entire application period (from one day to one week). For buccal patches and teeth strips, it is often desirable to use elastic polymer films, which exhibit no adhesion towards dry surfaces, but are highly tacky when applied to hydrated, soft mucosal surfaces and/or moistened solid tissue surfaces such as teeth. For wound dressings and other various purposes, in order to avoid skin damage upon patch removal, either water-soluble adhesives or insoluble hydrogel adhesives, which lose their adhesion under swelling in a large amount of water, are preferred. Face masks and some tooth whitening products best utilize hydrophilic polymer compositions in the form of aqueous or ethanol-water solutions, which become dry after placement on a surface, thereby forming an insoluble, polymer film that adheres to the underlying tissue surface, but does not adhere to other surfaces.

In order to effectively tailor the adhesive properties of polymer materials useful in pharmaceutical and cosmetic products, a design method has been developed based on molecular insight into mechanisms underlying the adhesive properties. As has been recently established, at a molecular level, the pressure-sensitive adhesion is due to coupling of two apparently incompatible types of molecular structures. This reveals that there is a fine balance between strong cohesive interaction energy and enhanced free volume. See, for example, Feldstein et al. (1999) *Polym. Mater. Sci. Eng.*, 81:465-466; Feldstein et al., *General approach to the molecular design of hydrophilic pressure-sensitive adhesives*, Proceed. $25^{th}$ Annual Meeting Adhesion Soc. and $2^{nd}$ World Congress on Adhesion and Relative Phenomena, February 2002, Orlando, Fla., vol. 1 (Oral Presentations), p. 292-294; and Chalykh et al. (2002) *J. Adhesion* 78(8):667-694.

The "free volume" property of the molecular structure of PSA polymers results in high tack at a macroscopic level and a liquid-like fluidity of the PSA material, which allows for a fast-forming adhesive bond. The "cohesive interaction energy" or "cohesion energy" property defines the cohesive toughness of the PSA polymer and provides the dissipation of detaching energy in the course of adhesive joint failure. Based on this finding, a general method for obtaining novel hydrophilic adhesives is described in U.S. Pat. No. 6,576,712 to Feldstein et al., which involves physically mixing non-adhesive, hydrophilic, high-molecular-weight polymers with appropriate short-chain plasticizers.

In various PSAs, different molecular structures provide proper amounts of cohesion energy and free volume, thereby defining the adhesive properties of the polymer materials. For instance, in acrylic PSAs, strong cohesive interaction energy is a result of mutual hydrophobic attraction of the alkyl radicals in side chains, whereas large free volume is due to either electrostatic repulsion of negatively charged carboxyl groups or a large volume of isoalkyl radicals in the side chains. In synthetic rubbers, a large free volume is obtained by adding high volume, low-density molecules of tackifying resins. In hydrophilic adhesives, when high molecular weight polyvinyl lactams (i.e. poly(N-vinyl-2-pyrrolidone) ("PVP") or polyvinyl caprolactame ("PVCap")) are blended with the short-chain polyethylene glycol ("PEG"), as described in U.S. Pat. No. 6,576,712, high cohesive strength results from hydrogen bonding between, for example, PVP carbonyl groups and complementary terminal hydroxyls of PEG, while the large free volume is due to the location of reactive groups at both ends of the PEG chains, which are of appreciable length and flexibility.

A proper balance between high cohesion energy and large free volume, which is responsible for adhesive properties of polymer materials, is achieved by evaluating the various PSA properties. For instance, the ratio between cohesion energy and free volume defines the value of glass transition temperature, Tg, and elasticity modulus, E, of a polymer. Higher cohesion energy and lower free volume, results in higher values for both Tg and E. It is well recognized that all PSAs demonstrate a Tg in the range of about −55 to −30° C. and an E≈$1-10^5$ Pa.

In U.S. Pat. No. 6,576,712, the hydrophilic polymers and plasticizer are capable of hydrogen bonding or electrostatic bonding to each other and are present in a ratio that optimizes key characteristics of the adhesive composition, such as adhesive strength, cohesive strength and hydrophilicity. The plasticizer has complementary reactive functional groups at both ends and when both terminal groups interact with complementary functional groups in the hydrophilic polymer, the plasticizer acts as a non-covalent crosslinker between the longer chains of hydrophilic polymer. In doing so, the plasticizer combines the plasticization effect with enhanced cohesive toughness of the PSA polymer blend. This molecular design method for tailoring new hydrophilic PSAs describes the adhesive capability of long-chain, high Tg hydrophilic polymers, as well as the ratio of hydrophilic polymer to plasticizer (cohesive enhancer), which provides the best adhesion.

When dry, the adhesives described in U.S. Pat. No. 6,576,712, e.g. the blends of high molecular weight PVP with oligomeric PEG ranging in molecular weight from 200 to 600 g/mol, provide rather low adhesion toward dry surfaces. Adhesion increases when the surface of a substrate is moistened or the adhesive absorbs water. The maximum adhesion is observed when the adhesive contains 5-10% of absorbed water. This is usually the case when the adhesive is exposed to an atmosphere having 50% relative humidity. Additionally, under direct contact with water, the adhesive dissolves. However, these adhesives not contain covalent crosslinks, and are thus not suitable for applications that require swellable yet water-insoluble adhesives. In particular, these prior art adhesives are less useful when increased adhesion is desired upon much more appreciable hydration levels (e.g., 15% of absorbed water and higher).

Therefore, while the prior art discloses polymers and hydrogel compositions that can be tailored with respect to cohesive strength, adhesive strength, tack, elasticity, and water swellability, it remains desirable to develop a molecular design method for preparing novel hydrophilic PSAs that focuses on balancing cohesive interaction energy and free volume at a molecular level.

In order to resolve these problems, this invention is directed to a method of obtaining water-insoluble, film-forming compositions by blending soluble polymers. While this has been attempted in the past, e.g., U.S. Pat. No. 5,597,873 to Chambers et al. and U.S. Pat. No. 5,306,504 to Lorenz et al. (mixing carboxyl-containing polymers with polyhydric alcohols and polyamines) and U.S. Pat. No. 4,771,105 to Shirai et al. and U.S. Pat. No. 5,726,250 to Zajaczkowski (crosslinking of polyacrylic acid "PAA" or the copolymers of acrylic acid with the salts of di- and trivalent metals ($Ca^{2+}$, $Al^{3+}$), all of these procedures are directed to the production of non-adhesive water absorbents by mixing techniques.

SUMMARY OF THE INVENTION

One aspect of the invention pertains to an adhesive composition comprising: a film-forming polymer selected from water-swellable water-insoluble polymers and water-soluble polymers; a ladder-like non-covalent crosslinker that contains complementary reactive functional groups in the repeating units of the backbone, and is capable of forming a ladder-like interpolymer complex with the film-forming polymer; and a carcass-like non-covalent crosslinker that contains complementary reactive functional groups at its ends, and is capable of forming a carcass-like complex with at least one of the film-forming polymer or the ladder-like non-covalent crosslinker; wherein the amount of the film-forming polymer is greater than the amount of the ladder-like non-covalent crosslinker or the amount of the carcass-like non-covalent crosslinker.

Another aspect of the invention relates to a method of selecting polymer components for use in an adhesive composition, comprising: (a) selecting a film-forming polymer; (b) selecting a ladder-like non-covalent crosslinker that contains complementary reactive functional groups in the repeating units of the backbone, and is capable of forming a ladder-like interpolymer complex with the film-forming polymer selected; and (c) selecting a carcass-like non-covalent crosslinker that contains complementary reactive functional groups at its ends, and is capable of forming a carcass-like complex with at least one of the film-forming polymer selected or the ladder-like non-covalent crosslinker selected; and wherein the amount of the film-forming polymer is greater than the amount of the ladder-like non-covalent crosslinker or the amount of the carcass-like non-covalent crosslinker.

Yet another aspect of the invention relates to a method of manufacturing an adhesive composition, comprising: (a) (i) selecting a film-forming polymer; (ii) selecting a ladder-like non-covalent crosslinker that contains complementary reactive functional groups in the repeating units of the backbone, and is capable of forming a ladder-like interpolymer complex with the film-forming polymer selected; and (iii) selecting a carcass-like non-covalent crosslinker that contains complementary reactive functional groups at its ends, and is capable of forming a carcass-like complex with at least one of the film-forming polymer selected or the ladder-like non-covalent crosslinker selected; and wherein the amount of the film-forming polymer is greater than the amount of the ladder-like non-covalent crosslinker or the amount of the carcass-like non-covalent crosslinker; (b) mixing the film-forming polymer, ladder-like non-covalent crosslinker and carcass-like non-covalent crosslinker; and (c) forming an adhesive composition by melt extrusion or solution casting.

The adhesive compositions produced by the methods of the invention provide a number of significant advantages relative to the prior art. In particular, these compositions provide one or more of the following advantages over the art: provide ease of handling; are readily modified during manufacture so that properties such as adhesion, absorption, translucence, and swelling can be controlled and optimized; can be formulated so that tack increases or decreases in the presence of moisture so that the composition is not sticky until moistened; minimize leakage of the active agent, when included, from the composition onto a mucosal surface (e.g., into the user's mouth); can be fabricated in translucent from, enabling the user to view the extent of whitening without removing the hydrogel composition from the teeth or mucosal surface; minimize damage to gums or mucous membranes in the mouth; can be worn comfortably and unobtrusively; are easily removed from the skin, teeth or mucosal surface, and leave no residue; are amenable to extended duration of wear or action; and can provide sustained and controlled release of a variety of active agents.

DETAILED DESCRIPTION OF THE INVENTION

I. Definitions and Nomenclature

Figure 1:
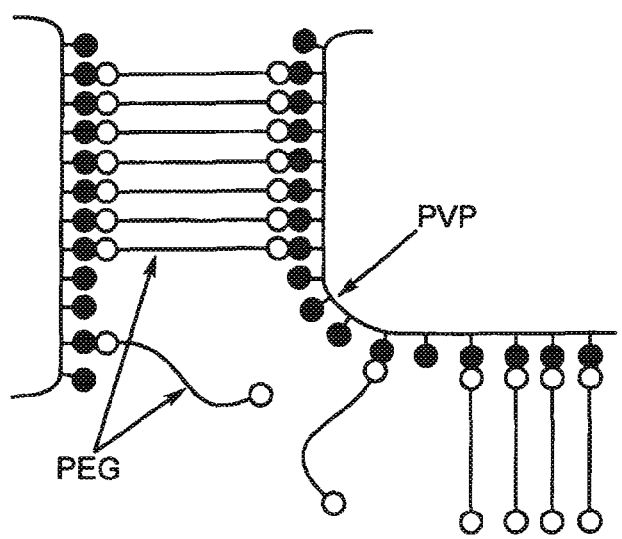
FIG. 1 is a schematic representation of a carcass-like PVP-PEG network complex. The PVP-PEG complex combines high cohesive toughness (due to PVP-PEG H-bonding) with a large free volume (resulting from considerable length and flexibility of PEG chains). In order to emphasize enhanced free volume in the PVP-PEG blend, this type of complex structure is defined as a "carcass-like" structure. The carcass-like structure of the complex results from the location of reactive functional groups at both ends of PEG short chains.

Before describing the present invention in detail, it is to be understood that unless otherwise indicated this invention is not limited to specific hydrogel materials or manufacturing processes, as such may vary. It is also to be understood that the terminology used herein is for the purpose of describing particular embodiments only, and is not intended to be limiting. It must be noted that, as used in this specification and the appended claims, the singular forms "a," "an," and "the" include plural referents unless the context clearly dictates otherwise. Thus, for example, reference to "a hydrophilic polymer" includes not only a single hydrophilic polymer but also a combination or mixture of two or more different hydrophilic polymers, reference to "a plasticizer" includes a combination or mixture of two or more different plasticizers as well as a single plasticizer, and the like.

In describing and claiming the present invention, the following terminology will be used in accordance with the definitions set out below.

The definitions of "hydrophobic" and "hydrophilic" polymers are based on the amount of water vapor absorbed by polymers at 100% relative humidity (rh). According to this classification, hydrophobic polymers absorb only up to 1 wt % of water at 100% relative humidity, while moderately hydrophilic polymers absorb 1-10 wt % of water, hydrophilic polymers are capable of absorbing more than 10 wt % of water, and hygroscopic polymers absorb more than 20 wt % of water. A "water-swellable" polymer is one that absorbs an amount of water greater than at least 25 wt % of its own weight, preferably at least 50 wt %, upon immersion in an aqueous medium.

The term "crosslinked" herein refers to a composition containing intramolecular and/or intermolecular crosslinks, whether arising through covalent or non-covalent bonding. "Non-covalent" bonding includes both hydrogen bonding and electrostatic (ionic) bonding.

The term "polymer" includes homopolymers, linear and branched polymer structures, and also encompasses crosslinked polymers as well as copolymers (which may or may not be crosslinked), thus including block copolymers, alternating copolymers, random copolymers, and the like. Those compounds referred to herein as "oligomers" are polymers having a molecular weight below about 1000 Da, preferably below about 800 Da.

The term "water-insoluble" refers to a polymer, compound or composition whose solubility in water is less than 5 wt %, preferably less than 3 wt %, more preferably less than 1 wt % (measured in water at 20° C.).

The term "hydrogel" is used in the conventional sense to refer to water-swellable polymeric matrices that can absorb a substantial amount of water to form elastic gels, where the "matrices" are three-dimensional networks of macromolecules held together by covalent or non-covalent crosslinks. Upon placement in an aqueous environment, dry hydrogels swell to the extent allowed by the degree of cross-linking.

The term "hydrogel composition" refers to a composition that either contains a hydrogel or is entirely composed of a hydrogel. As such, "hydrogel compositions" encompass not only hydrogels per se but also compositions that comprise a hydrogel and one or more non-hydrogel components or compositions, e.g., hydrocolloids, which contain a hydrophilic component (which may contain or be a hydrogel) distributed in a hydrophobic phase.

The terms "tack" and "tacky" are qualitative. However, the terms "substantially nontacky," "slightly tacky," and "tacky," as used herein, may be quantified using the values obtained in a PKI tack determination, a TRBT tack determination, or a PSA tack determination/Polyken Probe (Solutia, Inc.). The term "substantially nontacky" means a hydrogel composition that has a tack value that is less than about 25 g-cm/sec, "slightly tacky" means a hydrogel composition that has a tack value in the range of about 25 g-cm/sec to about 100 g-cm/sec, and "tack" means a hydrogel composition that has a tack value of at least 100 g-cm/sec.

The term "pressure sensitive adhesive" (PSA) relates to the polymer materials, which form a strong adhesive bond to any surface with application of very slight external pressure over a short period of time (e.g., 1-5 seconds).

The term "bioadhesive" means a hydrogel that exhibits a pressure-sensitive character of adhesion toward highly hydrated biological surfaces such as mucosal tissue.

The term "complex" or "interpolymer complex" refers to the association of macromolecules of two or more complementary polymers that forms as a result of favorable interactions between their macromolecules. In general, the interpolymer complex between the film forming polymer, the ladder-like crosslinker and the carcass-like crosslinker is formed by hydrogen bonding, electrostatic bonding, ionic bonding, or a combination thereof.

The term "ladder-like" defines the complex or the mechanism of complexation leading to the associate of complementary macromolecules, wherein specific interaction occurs between the complementary functional groups in the repeating units of polymeric backbones. Due to entropic reasons, functional groups are linked together not separately but in a cooperative manner, thus forming sequences of relatively short and tough bonds. The schematic structure of this complex shown in FIG. 2 resembles a ladder.

The term "carcass-like" defines the complex or the mechanism of complexation leading to the association of complementary macromolecule and oligomeric chains, wherein specific interaction occurs between the complementary functional groups in the repeating units of the backbone of the longer polymer chain and the reactive groups at the both ends of the shorter oligomeric chain. In contrast to the ladder-like complex, the term "carcass-like" emphasizes that the crosslinks between the longer polymer chains are of appreciable length and the density of network formed by this way is much lower, as shown schematically in FIG. 1.

Figure 3:
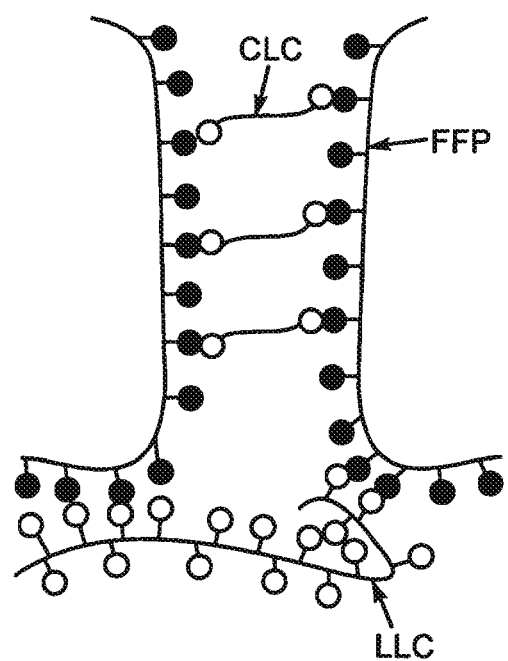
FIG. 3 demonstrates a schematic representation of an interpolymer complex combining carcass-like and ladder-like types of crosslinking. "FFP" represents a film-forming polymer, "CCL" represents a carcass-like non-covalent crosslinker, and "LLC" represents a ladder-like non-covalent crosslinker.

Both the ladder-like and carcass-like complexes are crosslinked due to specific interactions between reactive groups in complementary macromolecules and thus represent "networks". In the context of present invention the term "network" is used interchangeably with the term "complex", but refers more specifically to the supramolecular structure of the interpolymer complex, as shown schematically in FIG. 3.

The terms "active agent," "pharmacologically active agent" and "drug" are used interchangeably herein to refer to a chemical material or compound that induces a desired pharmacological or physiological effect, and includes agents that are therapeutically effective, prophylactically effective, or cosmeceutically effective. The terms also encompass pharmaceutically acceptable, pharmacologically active derivatives and analogs of those active agents specifically mentioned herein, including, but not limited to, salts, esters, amides, prodrugs, active metabolites, inclusion complexes, analogs, and the like. When the terms "active agent," "pharmacologically active agent" and "drug" are used, it is to be understood that both the active agent per se as well as pharmaceutically acceptable, pharmacologically active salts, esters, amides, prodrugs, active metabolites, inclusion complexes, analogs, etc., are included.

The term "effective amount" or "a cosmeceutically effective amount" of a cosmeceutically active agent is meant a nontoxic but sufficient amount of a cosmeceutically active agent to provide the desired cosmetic effect. The term "effective amount" or "a therapeutically effective amount" of a drug or pharmacologically active agent is intended to mean a nontoxic but sufficient amount of the drug or agent to provide the desired therapeutic effect. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation. Furthermore, the exact "effective" amount of an active agent incorporated into a composition or dosage form of the invention is not critical, so long as the concentration is within a range sufficient to permit ready application of the formulation so as to deliver an amount of the active agent that is within a therapeutically effective range.

The term "transdermal" drug delivery means administration of an active agent to the skin or mucosa of an individual so that the drug passes through the skin tissue and into the individual's blood stream. Unless otherwise indicated, the term "transdermal" is intended to include "transmucosal" drug administration, i.e., administration of a drug to the mucosal (e.g., sublingual, buccal, vaginal, rectal, urethral) surface of an individual so that the drug passes through the mucosal tissue and into the individual's blood stream.

The term "topical administration" is used in its conventional sense to mean delivery of an active agent to a body surface, such as, the skin or mucosa, as in, for example, topical drug administration in the prevention or treatment of various skin disorders, the application of cosmetics (including moisturizers, masks, sunscreens, etc.), and the like. Topical administration, in contrast to transdermal administration, provides a local rather than a systemic effect.

The term "surface" or "body surface" is used to refer to any surface located on the human body or within a body orifice. Thus, a "body surface" includes, by way of example, teeth, skin or mucosal tissue, including the interior surface of body cavities that have a mucosal lining. Unless otherwise indicated, the term "skin" as used herein should be interpreted as including mucosal tissue and vice versa. Similarly, when the term "transdermal" is used herein, as in "transdermal drug administration" and "transdermal drug delivery systems," it is to be understood that unless explicitly indicated to the contrary, both "transmucosal" and "topical" administration and systems are intended as well.

II. Adhesive Compositions-Main Components

It is desirable to obtain water-swellable, hydrophilic adhesive compositions (adhesive hydrogels) that are capable to form homogeneous films either upon casting a solution to backing layer followed by drying, or under external pressure or by means of extrusion. Preferably, such compositions are also water-insoluble. The film-forming capability is optimal when the blend is free of covalent crosslinks. Blending specific polymers provides a convenient way to obtain composite materials with specifically tailored properties, since the properties of the blend are typically intermediate between those of the unblended components when the components are immiscible or partly miscible. In order to make the composite insoluble in water, water-insoluble materials are usually mixed with water-soluble materials. When this is done, however, a phase separation can often occur that does not favor adhesion. Moreover, the insolubility of blend components may hamper the procedure of blend preparation, which often involves the dissolution of all the components in a common solvent, followed by casting the solution and drying.

Preparation of polymer composite materials whose properties are new and untypical of the individual components requires a high degree of skill. This challenge may be resolved if the individual blend components are capable of strong favorable interactions with each other. Typically, such interaction is due to hydrogen, electrostatic or ionic bonding. In this instance mixing of two or more soluble polymers provides a ladder-like complex, schematically shown in FIG. 2 that is swellable, but insoluble or partly soluble.

In order to resolve these problems, this invention is directed to a method of obtaining water-insoluble, film-forming compositions by blending soluble polymers, more specifically by blending hydrophilic polymers with complementary macromolecules that are capable of hydrogen bonding, electrostatic or ionic bonding.

At least one component of the blend is a film-forming polymer, at least one component of the blend is a ladder-like non-covalent crosslinker of the film-forming polymer, and at least one component of the blend is a carcass-like non-covalent crosslinker of the film-forming polymer. Key to the invention is that the film-forming polymer is present in a higher concentration than either of the cross-linkers. This concentration is what determines the film-forming characteristics. Therefore, while there may be materials that are suitable for use as either the film-forming polymer or as the ladder-like non-covalent crosslinker, their function and role in the composition will be determined by the amount of material present in the composition.

For example, poly-acids such as acrylate polymers bearing carboxyl proton donating functional groups or polyols bearing hydroxyl proton donating functional groups and proton-accepting polymers such as poly(N-vinyl lactams) or polyamines are suited for use as both the film-forming polymer or as the ladder-like non-covalent crosslinker. In a composition having a greater amount of an acrylate or another proton donating polymer relative to the amount of a poly(N-vinyl lactam), the acrylate polymer serves as the film-forming polymer and the poly(N-vinyl lactam) or polyamine or another proton-accepting polymer serves as the ladder-like crosslinker. Similarly, in a composition having a greater amount of a poly(N-vinyl lactam) or polyamine relative to the amount of an acrylate polymer, the poly(N-vinyl lactam) or polyamine serves as the film-forming polymer and the acrylate polymer serves as the ladder-like crosslinker.

Thus, one embodiment of the invention is a method of selecting polymer components for use in an adhesive composition. The method first involves selecting a film-forming polymer. Then, a ladder-like non-covalent crosslinker is selected that (1) contains complementary reactive functional groups in the repeating units of the backbone, and (2) is capable of forming a ladder-like interpolymer complex with the film-forming polymer selected. Finally, a carcass-like non-covalent crosslinker is selected that (1) contains complementary reactive functional groups at its ends, and (2) is capable of forming a carcass-like complex with at least one of the film-forming polymer selected or the ladder-like non-covalent crosslinker selected. The carcass-like non-covalent crosslinker is preferably compatible or at least partially compatible with both the film-forming polymer and the ladder-like non-covalent crosslinker. The method involves not only the aforementioned material selections, but also involves selecting the quantities of materials used. In particular, the amount of the film-forming polymer is greater than the amount of the ladder-like non-covalent crosslinker or the amount of the carcass-like non-covalent crosslinker. The method may also comprise the steps of selecting one or more additional ladder-like non-covalent crosslinkers and/or selecting one or more additional carcass-like non-covalent crosslinkers. Such additional crosslinkers will be selected based upon the same or similar criteria as the first crosslinkers, i.e., complementarity and ability to form the desired complex.

Typically the composition will contain one film forming polymer, but may contain more than one ladder-like crosslinker and/or more than one carcass-like crosslinker.

The adhesion profile of the water-insoluble, film-forming compositions of the invention can be tailored based on materials, the composition ratio and the extent of water in the blend. The ladder-like crosslinker and its ratio to the amount of film-forming polymer is selected so as to provide the desired adhesion profile with respect to hydration. Generally, the compositions that are relatively slightly crosslinked through comparatively loose hydrogen bonds and demonstrating a large free volume, provide initial tack in the dry state. As the degree of crosslinking and cohesive strength of the network in the interpolymer complex moves above some critical value, the energy of cohesion dominates under free volume and such compositions are usually non-tacky in the dry state. However, as the free volume is increased in this blend, the adhesion immediately appears. Since water is a good plasticizer for hydrophilic polymers, absorption of water can lead to the improvement of adhesion. Since electrostatic bonds are appreciably stronger than the hydrogen ones, the cohesion in the blends of polymers bearing carboxyl groups is usually higher than in materials made of polymers having hydroxyl groups. Adhesion in such blends appears under higher concentration of absorbed water. Flexible polymers provide higher cohesion than the polymers with rigid chains. As an example, for the blends of PVP as film-forming polymer, when the ladder-like crosslinker is a rigid-chain cellulose ester bearing OH groups or cellulose, the composition is generally tacky prior to contact with water (e.g., with a moist surface) but gradually loses tack as the composition absorbs moisture. When the ladder-like crosslinker is an acrylate polymer or copolymer with carboxylic groups, a composition is provided that is generally substantially nontacky prior to contact with water, but becomes tacky upon contact with a moist surface.

A. Film-Forming Polymers

The film-forming polymers are present in the adhesive composition in a higher concentration than the amount of the ladder-like crosslinker or the amount of the carcass-like crosslinker and provides film-forming properties. Typically, the amount of the film-forming polymer will range from about 20-95 wt % of the composition, while the amount of the ladder-like crosslinker will range from about 0.5-40 wt % and the amount of the carcass-like crosslinker will range from about 0.5-60 wt %. The balance of the composition can be made up of components such as plasticizers and tackifiers, water or other solvents, active agents, pH regulators, and so forth, as are described below.

Typically, the film-forming polymers are relatively high molecular weight polymers and will have a molecular weight within the range of about 20,000 to 3,000,000, preferably within the range of 100,000 to 2,000,000, more typically in the range of approximately 500,000 to 1,500,000.

The film-forming polymer is capable of forming hydrogen or electrostatic bonds with the functional repeating units of the ladder-like crosslinker and the terminal functional groups of the carcass-like crosslinker. Suitable film-forming polymers include, by way of illustration and not limitation, hydrophilic polymers, water-swellable water-insoluble polymers, water-soluble polymers, copolymers of hydrophilic and hydrophobic monomers, and combinations thereof.

1. Hydrophilic Polymers

Exemplary synthetic hydrophilic polymers include, by way of illustration and not limitation, poly(dialkyl aminoalkyl acrylates), poly(dialkyl aminoalkyl methacrylates), polyamines, polyvinyl amines, poly(alkylene imines), substituted and unsubstituted acrylic and methacrylic acid polymers such as polyacrylic acids (PAAs) and polymethacrylic acids (PMAs), polymaleic acids, polysulfonic acids, poly(N-vinyl lactams), polyalkylene oxides, polyvinyl alcohols, polyvinyl phenols, poly(hydroxyalkyl acrylates), poly(hydroxyalkyl methacrylates), poly(N-vinyl acrylamides), poly(N-alkylacrylamides), homopolymers, copolymers, and combinations thereof, as well as copolymers with other types of hydrophilic monomers (e.g. vinyl acetate).

Exemplary natural hydrophilic polymers include, by way of illustration and not limitation, polar derivatives of cellulose containing hydroxyl and carboxyl groups, such as carboxymethylcellulose and hydroxypropylmethylcellulose phthalate, alginic acid, chitosan and gelatin.

Preferred hydrophilic polymer film-forming polymers are synthetic polymers, and include poly(dialkyl aminoalkyl acrylates); poly(dialkyl aminoalkyl methacrylates); polyacrylic acids; polymethacrylic acids; polymaleic acids; polyvinylamines; poly(N-vinyl lactams) such as poly(N-vinyl pyrrolidone) (e.g., poly(N-vinyl-2-pyrrolidone)), poly(N-vinyl-2-valerolactam), and poly(N-vinyl caprolactam) (e.g., poly(N-vinyl-2-caprolactam)); polyalkylene oxides such as polyethylene oxide (PEO) and polypropylene oxide; polyvinyl alcohols; polyvinyl phenols; and poly(hydroxyalkyl acrylates) such as poly(hydroxyethyl methacrylate) (Poly-HEMA), poly(hydroxyethyl acrylate), and copolymers thereof.

Other suitable hydrophilic polymers include repeating units derived from an N-vinyl lactam monomer, a carboxy vinyl monomer, a maleic acid monomer, a dialkyl aminoalkyl acrylate or a dialkyl aminoalkyl methacrylate monomer, ethylene oxide monomer, a vinyl ester monomer, an ester of a carboxy vinyl monomer, a vinyl amide monomer, and/or a hydroxy vinyl monomer. Such polymers include, by way of example, polyvinylamines, polyacrylic acids, polymethacrylic acids, polymaleic acids, poly(N-vinyl lactams), poly(N-vinyl acrylamides), poly(N-alkylacrylamides), polyethylene oxides, polyvinyl alcohols, and polyvinyl phenol.

Poly(N-vinyl lactams) useful herein are preferably non-crosslinked homopolymers or copolymers of N-vinyl lactam monomer units, with N-vinyl lactam monomer units representing the majority of the total monomeric units of a poly (N-vinyl lactams) copolymer. Preferred poly(N-vinyl lactams) for use in conjunction with the invention are prepared by polymerization of one or more of the following N-vinyl lactam monomers: N-vinyl-2-pyrrolidone; N-vinyl-2-valerolactam; and N-vinyl-2-caprolactam. Nonlimiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

Poly(N-alkylacrylamides) include, by way of example, poly(methacrylamide) and poly(N-isopropyl acrylamide) (PNIPAM).

Polymers of carboxy vinyl monomers are typically formed from acrylic acid, methacrylic acid, crotonic acid, isocrotonic acid, itaconic acid and anhydride, a 1,2-dicarboxylic acid such as maleic acid or fumaric acid, maleic anhydride, or mixtures thereof, with preferred hydrophilic polymers within this class including polyacrylic acid and polymethacrylic acid, with polyacrylic acid most preferred.

Preferred hydrophilic polymers herein are the following: poly(N-vinyl lactams), particularly poly(N-vinyl pyrrolidone) (PVP) and poly(N-vinyl caprolactam) (PVCap); poly (N-vinyl acetamides), particularly polyacetamide per se; polymers of carboxy vinyl monomers, particularly polyacrylic acid and polymethacrylic acid; polymaleic acids; and copolymers and blends thereof. PVP and PVCap are particularly preferred.

2. Water-Swellable Water-Insoluble Polymers

Exemplary water-swellable water-insoluble polymers include, by way of illustration and not limitation, cellulose derivatives such as cellulose esters, and acrylate-based polymers or copolymers, as well as combinations thereof. The water-swellable water-insoluble polymer is capable of at least some degree of swelling when immersed in an aqueous liquid but is insoluble in water. The polymer may be comprised of a cellulose ester, for example, cellulose acetate, cellulose acetate propionate (CAP), cellulose acetate butyrate (CAB), cellulose propionate (CP), cellulose butyrate (CB), cellulose propionate butyrate (CPB), cellulose diacetate (CDA), cellulose triacetate (CTA), or the like. These cellulose esters are described in U.S. Pat. Nos. 1,698,049, 1,683,347, 1,880,808, 1,880,560, 1,984,147, 2,129,052, and 3,617,201, and may be prepared using techniques known in the art or obtained commercially. Commercially available cellulose esters suitable herein include CA 320, CA 398, CAB 381, CAB 551, CAB 553, CAP 482, CAP 504, all available from Eastman Chemical Company, Kingsport, Tenn. Such cellulose esters typically have a number average molecular weight of between about 10,000 and about 75,000.

Generally, the cellulose ester comprises a mixture of cellulose and cellulose ester monomer units; for example, commercially available cellulose acetate butyrate contains cellulose acetate monomer units as well as cellulose butyrate monomer units and unesterified cellulose monomer units, while cellulose acetate proprionate contains monomer units such as cellulose proprionate. Preferred cellulose esters herein are cellulose acetate propionate compositions and cellulose acetate butyrate compositions having the butyryl, propionyl, acetyl, and unesterified (OH) cellulose content as indicated below:

|  |  | Acetyl (%) | OH (%) | MW (g/mole) | $T_g$ (°C.) | $T_m$ (°C.) |
|---|---|---|---|---|---|---|
| Cellulose Acetate Butyrate | 17-52% Butyrate | 2.0-29.5 | 1.1-4.8 | 12,000-70,000 | 96-141 | 130-240 |
| Cellulose Acetate Propionate | 42.5-47.7% Propionate | 0.6-1.5 | 1.7-5.0 | 15,000-75,000 | 142-159 | 188-210 |

The preferred molecular weight, glass transition temperature ($T_g$) and melting temperature ($T_m$) are also indicated. Also, suitable cellulosic polymers typically have an inherent viscosity (I.V.) of about 0.2 to about 3.0 deciliters/gram, preferably about 1 to about 1.6 deciliters/gram, as measured at a temperature of 25° C. for a 0.5 gram sample in 100 ml of a 60/40 by weight solution of phenol/tetrachloroethane. When prepared using a solvent casting technique, the water-swellable water-insoluble polymer should be selected to provide greater cohesive strength and thus facilitate film forming (generally, for example, cellulose acetate propionate tends to improve cohesive strength to a greater degree than cellulose acetate butyrate).

Other cellulose derivatives include cellulosic polymers containing hydroxyalkyl cellulose or carboxyalkyl cellulose monomer units.

Other preferred water-swellable water-insoluble polymers are acrylate-based polymers or copolymers, generally formed from acrylic acid, methacrylic acid, methyl acrylate, ethyl acrylate, methyl methacrylate, ethyl methacrylate, and/or other vinyl monomers. Several of these are also classified as hydrophilic polymers, above. Suitable acrylate polymers are those copolymers available under the tradename "Eudragit"

from Rohm Pharma (Germany). The Eudragit® series E, L, S, RL, RS and NE copolymers are available solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are Eudragit L 30D-55 and Eudragit L 100-55 (the latter copolymer is a spray-dried form of Eudragit L 30D-55 that can be reconstituted with water). The molecular weight of the Eudragit L 30D-55 and Eudragit L 100-55 copolymer is approximately 135,000 Da, with a ratio of free carboxyl groups to ester groups of approximately 1:1. The Eudragit L 100-55 copolymer is generally insoluble in aqueous fluids having a pH below 5.5. Another particularly suitable methacrylic acid-methyl methacrylate copolymer is Eudragit S 100, which differs from Eudragit L 30D-55 in that the ratio of free carboxyl groups to ester groups is approximately 1:2. Eudragit S 100 is insoluble at pH below 5.5, but unlike Eudragit L 30D-55, is poorly soluble in aqueous fluids having a pH in the range of 5.5 to 7.0. This copolymer is soluble at pH 7.0 and above. Eudragit L 100 may also be used, which has a pH-dependent solubility profile between that of Eudragit L 30D-55 and Eudragit S 100, insofar as it is insoluble at a pH below 6.0. It will be appreciated by those skilled in the art that Eudragit L 30D-55, L 100-55, L 100, and S 100 can be replaced with other acceptable polymers having similar pH-dependent solubility characteristics. Other suitable acrylate polymers are those methacrylic acid/ethyl acrylate copolymers available under the tradename "Kollicoat" from BASF AG (Germany). For example, Kollicoat MAE has the same molecular structure as Eudragit L 100-55.

When the water-swellable water-insoluble polymer is an acrylic acid or acrylate polymer, a hydrogel is provided that can be reversibly dried, i.e., after removal of water and any other solvents, the dried hydrogel may be reconstituted to its original state by addition of water. In addition, hydrophilic hydrogels prepared with an acrylic acid/acrylate water-swellable polymer are generally substantially nontacky prior to contact with water, but become tacky upon contact with a moist surface, such as is found in the interior of the mouth, such as on the surface of the teeth. This property of being nontacky prior to contact with water enables positioning or repositioning on a chosen surface before, or as the hydrogel becomes tacky. For example, once hydrated, the hydrogel becomes tacky and can adhere to a surface such as a tooth or mucosal surface.

In addition, acrylate-containing compositions can generally provide swelling in the range of about 400% to 1500% upon immersion of the composition in water or other aqueous liquid, at a pH of less than 5.5-6.0, although the ratio of the acrylate polymer to the other materials can be selected such that the rate and extent of swelling in an aqueous environment has a predetermined pH-dependence. This feature also provides for retroactive incorporation of whitening agents or other active agents, such as loading the composition with peroxide, peroxy acids, chlorites, stabilizers, flavoring agents, etc.

By contrast, incorporating a cellulose ester as the water-swellable water-insoluble polymer renders the composition tacky prior to application to a moist surface, but nontacky upon absorption of water. It will be appreciated that such a composition may be desirable when a decrease in tack is desired for ultimate removal of the product from the teeth.

3. Water-Soluble Polymers

Exemplary water-soluble polymers include, by way of illustration and not limitation, water-soluble cellulose derived polymers; homopolymer and copolymers of vinyl alcohols; homopolymer and copolymers of vinyl phenols; homopolymer and copolymers of ethylene oxides; homopolymer and copolymers of maleic acid; collagen; gelatin; alginates; starches; and naturally occurring polysaccharides; and combinations thereof. The polymers include Exemplary water-soluble cellulose derived polymers include hydroxypropylcellulose, hydroxyethylcellulose, methylcellulose, hydroxypropyl methylcellulose, carboxymethylcellulose, sodium carboxymethylcellulose, hydratecellulose (cellophane), and hydroxypropylmethylcellulose, and combinations thereof.

Exemplary naturally occurring polysaccharides include agars of various origin such as gum agar; alginates such as alginic acid, salts of alginic acid (e.g., calcium alginate, potassium alginate, sodium alginate), and derivatives of alginic acid (e.g. propylene glycol alginate, Kelcoloid®, Monsanto); carrageenans including kappa-, iota- and lambda carrageenans; chitin; chitosan; glucomannan; gellan gum (Kelcogel®, Monsanto); gelatin; gum guar (TIC Gums); gum arabic; gum ghatti; gum karaya; gum tragacanth; locust bean gum; pectins such as pectin and amylopectin; pullulan; starches and starch derivatives such as potato starch acetate, Clearam® CH10, Roquette; tamarind gum; xanthans such as xanthan gum; and combinations thereof.

Exemplary water-soluble maleic acid polymers include those available under the tradename Gantrez® from International Specialty Products. Gantrez® products are a family of synthetic copolymers of methylvinyl ether and maleic anhydride. Gantrez AN are copolymers of methylvinyl ether and maleic anhydride. Gantrez S series represent the copolymers of methylvinyl ether and maleic acid, such as Gantrez S-97. Gantrez ES is the half ester form of maleic acid and represent a range of methylvinyl ether and maleic acid copolymers with different alkyl chain lengths and molecular weights. Thus Gantrez ES-225 and Gantrez ES-425 are monoethyl and monobutyl esters of the copolymers of methylvinyl ether and maleic acid.

B. Ladder-Like Non-Covalent Crosslinkers

The ladder-like non-covalent crosslinker of the film-forming polymer is preferably a long chain polymer containing complementary reactive functional groups in the repeating units of the backbone, and is capable of forming a ladder-like interpolymer complex with the hydrophilic, high molecular weight film-forming polymer. This complex can be water-soluble or water-insoluble, but is preferably water-insoluble.

One function of the ladder-like crosslinker is to provide insolubility and limited swelling to the blend. In essence, the ladder-like crosslinker can serve as a gel-forming agent. Suitable complementary reactive functional groups for the ladder-like crosslinker, include hydroxyl, carboxyl, phenolic, sulfo, and amino groups, all of which are capable of non-covalently crosslinking the hydrophilic polymer blend. Typically, these polymers will have a length within the range of about 10,000 to 1,000,000 g/mol, optimally 100,000-300,000 g/mol. It may be desirable to select a ladder-like crosslinker that has a lower molecular weight than that of the film-forming polymer.

Exemplary long chain polymers suitable for use as the ladder-like crosslinker include, by way of illustration and not limitation, hydrophilic polymers, water-swellable water-insoluble polymers, and water-soluble polymers, as described above for use as film-forming polymers.

As noted above, the same materials may be used as either the film-forming polymer or as the ladder-like non-covalent crosslinker since both the film-forming polymer and the ladder-like non-covalent crosslinker represent the same class of polymers, which bear reactive groups, capable of hydrogen, electrostatic or ionic bonding, in the repeating units of polymer backbones. Their function and role in the composition will be determined by the amount of material present in the composition, where the material present in the greatest quantity functions as the film-forming polymer, i.e., the difference between the film-forming polymer and its ladder-like crosslinker is an issue of their concentration. The predominant component is typically referred to as the film-forming polymer, while the minor component is referred to as the ladder-like non-covalent crosslinker. Thus, for the purposes of present invention, it is not critical what polymer serves as the major film-forming polymer, and what serves as the ladder-like non-covalent crosslinker.

Nevertheless, the complementarity of the film-forming polymer and the ladder-like non-covalent crosslinker is an important aspect of the invention. A list of exemplary complementary functional groups and the types of bonding for the film-forming polymer and the ladder-like non-covalent crosslinker is presented below. A distinctive feature of hydrogen bonding between proton donating and proton accepting complementary groups is that both the reactive groups and the product of their interaction bear no electric charge. Electrostatic bonding is the interaction of proton donating and proton accepting groups, which are initially uncharged, with the formation of ionic bond. And lastly, ionic bonding is the interaction of oppositely charged groups with the formation of ionic bond.

| Complementary groups | | Type of Bonding |
|---|---|---|
| —COOH, —PhOH, —SO$_3$H | —NH$_2$, —NHR, —NR$_2$, —OH, —C—O—C—, —CONH$_2$, —CONHR, —CONR$_2$ | Electrostatic Hydrogen |
| —COO$^-$ | —NH$_3^+$, —NH$_2$R$^+$, —NHR$_2^+$, —NR$_3^+$ | Ionic |
| —OH | —COOH, —SO$_3$H, —CONH$_2$, —CONHR, —CONR$_2$ | Hydrogen |

—R and -Ph represent alkyl or phenyl radicals, respectively

The composition may also contain a second ladder-like non-covalent crosslinker. Like the first ladder-like crosslinker, the second ladder-like crosslinker also contains complementary reactive functional groups in the repeating units of the backbone. However, the second ladder-like crosslinker is capable of forming a ladder-like interpolymer complex with the film-forming polymer or the first ladder-like crosslinker.

C. Carcass-Like Non-Covalent Crosslinkers

The carcass-like non-covalent crosslinker preferably contains complementary reactive functional groups at its ends, and is capable of forming a carcass-like complex with at least one of the film-forming polymer or the ladder-like non-covalent crosslinker. Typically, the carcass-like non-covalent crosslinker is a hydrophilic oligomer with reactive groups at both ends of its short chain.

One function of the carcass-like crosslinker is to impart the adhesive properties to the hydrophilic polymer blend. Suitable complementary reactive functional groups for the carcass-like crosslinker, include hydroxyl, carboxyl and amino groups, all of which are capable of non-covalently crosslinking the hydrophilic polymer blend.

Preferably, the carcass-like non-covalent crosslinker is terminated with hydroxyl groups, amino or carboxyl groups. Generally, the carcass-like non-covalent crosslinker will have a molecular weight in the range from about 45 to about 800, preferably in the range of about 45 to about 600.

Exemplary carcass-like crosslinkers include, by way of illustration and not limitation, monomeric and oligomeric alkylene glycols comprising about 1-20 alkylene oxide units in their chains such as polyalkylene glycols (e.g., ethylene glycol, 1,2-propylene glycol (PG) and polyethylene glycol), including carboxyl-terminated oligomeric alkylene glycols such as carboxyl-terminated polyalkylene glycols, and amino-terminated oligomeric alkylene glycols such as amino-terminated polyalkylene glycols; polyalcohols such as low molecular weight polyhydric alcohols (e.g. glycerol or sorbitol); alkane diols from butane diol to octane diol; carbonic diacids; ether alcohols (e.g., glycol ethers); and poly (alkylene glycol diacids), and combinations thereof.

Preferred carcass-like crosslinkers are oligo-alkylene glycols such as polyethylene glycol (PEG), carboxyl-terminated oligo-alkylene glycols such as carboxyl-terminated poly(ethylene glycols), and polyhydric alcohols. Particularly preferred crosslinkers are low molecular weight polyalkylene glycols (molecular weight 200-600) such as polyethylene glycol 400.

The carcass-like crosslinker may also serve as a low molecular weight plasticizer, for example, when the carcass-like crosslinker is a compound such as polyethylene glycol 400. Such carcass-like crosslinker plasticizers would preferably be miscible with the other components and be able to decrease the glass transition temperature (Tg) and elasticity modulus of the composition. Alternatively, a different compound can be included as a low molecular weight plasticizer.

The carcass-like non-covalent crosslinker typically has a glass transition temperature $T_g$ in the range of about $-100°$ C. to about $-30°$ C. and a melting temperature $T_m$ lower than about $20°$ C. The carcass-like non-covalent crosslinker may be also amorphous. The difference between the $T_g$ values of the film-forming polymer and the ladder-like non-covalent crosslinker the $T_g$ value of the carcass-like non-covalent crosslinker is preferably greater than about $50°$ C., more preferably greater than about $100°$ C., and most preferably in the range of about $150°$ C. to about $300°$ C. The film-forming polymer, ladder-like non-covalent crosslinker and carcass-like non-covalent crosslinker should be compatible, i.e. capable of forming a homogeneous blend.

As discussed in U.S. Patent Publication No. 2002/0037977 to Feldstein et al., the ratio of the carcass-like non-covalent crosslinker to the other components of the composition can affect both adhesive strength and the cohesive strength. For example, the carcass-like non-covalent crosslinker decreases the glass transition of the film-forming polymer/carcass-like non-covalent crosslinker blend to a greater degree than predicted by the Fox equation, which is given by equation (1)

$$\frac{1}{T_{gpredicated}} = \frac{w_{pol}}{T_{gpol}} + \frac{w_{pl}}{T_{gpl}} \qquad (1)$$

where $T_{g\,predicted}$ is the predicted glass transition temperature of the blend, $w_{pol}$ is the weight fraction of the film-forming polymer in the blend, $w_{pl}$ is the weight fraction of the carcass-like non-covalent crosslinker in the blend, $T_{g\,pol}$ is the glass transition temperature of the film-forming polymer, and $T_{g\,pl}$ is the glass transition temperature of the carcass-like non-covalent crosslinker. As also explained in that patent application, an adhesive composition having optimized adhesive and cohesive strength can be prepared by selecting the film-forming polymer and carcass-like non-covalent crosslinker, and their relative amounts to give a predetermined deviation from $T_{g\ predicted}$. Generally, to maximize adhesion, the predetermined deviation from $T_{g\ predicted}$ will be the maximum negative deviation, while to minimize adhesion, any negative deviation from $T_{g\ predicted}$ is minimized.

As noted above, the composition may also contain a second ladder-like non-covalent crosslinker that is capable of forming a ladder-like interpolymer complex with the film-forming polymer or the first ladder-like crosslinker. When a second ladder-like crosslinker is included, the carcass-like non-covalent crosslinker can also be capable of forming a carcass-like complex with the second ladder-like crosslinker.

For example, an acrylate polymer (Eudragit E 100) can be selected as the film-forming polymer. The first ladder-like crosslinker can be Eudragit L-100-55, which forms a ladder-like interpolymer complex with the Eudragit E 100 film-forming polymer. The second ladder-like crosslinker can be PVP, which forms a ladder-like interpolymer complex with the Eudragit L-100-55 first ladder-like crosslinker. The carcass-like crosslinker can be PEG, which forms a carcass-like complex with the second ladder-like crosslinker PVP.

D. Exemplary Adhesive Compositions

An illustrative composition includes poly(N-vinyl-2-pyrrolidone) ("PVP") as the film-forming polymer and polyethylene glycol ("PEG") as the carcass-like non-covalent crosslinker. Mixing a PVP-PEG adhesive blend with a ladder-like non-covalent crosslinker that is a moderately hydrophilic or water-insoluble polymer results in the decrease of blend hydrophilicity and dissolution rate. In order to decrease the dissolution rate further or to obtain insoluble mixtures, the PVP-PEG blend can be mixed with polymers that bear complementary (with respect to PVP) reactive functional groups in their repeating units. Since the PVP contains proton-accepting carbonyl groups in its repeating units, the complementary functional groups are preferably proton-donating, hydroxyl or carboxyl groups. Thus, for use with PVP and PEG, suitable ladder-like non-covalent crosslinkers are long chain polymers such as polyvinyl alcohols, polyacrylic acids, polymethacrylic acids, polymaleic acids, homo- and co-polymers thereof, as well as sulfonic acid and alginic acid.

Another illustrative composition uses a copolymer of methacrylic acid and methyl methacrylate as the ladder-like non-covalent crosslinker with the PVP-PEG noted above. This composition is used to facilitate in understanding the principles of the invention.

Figure 2:
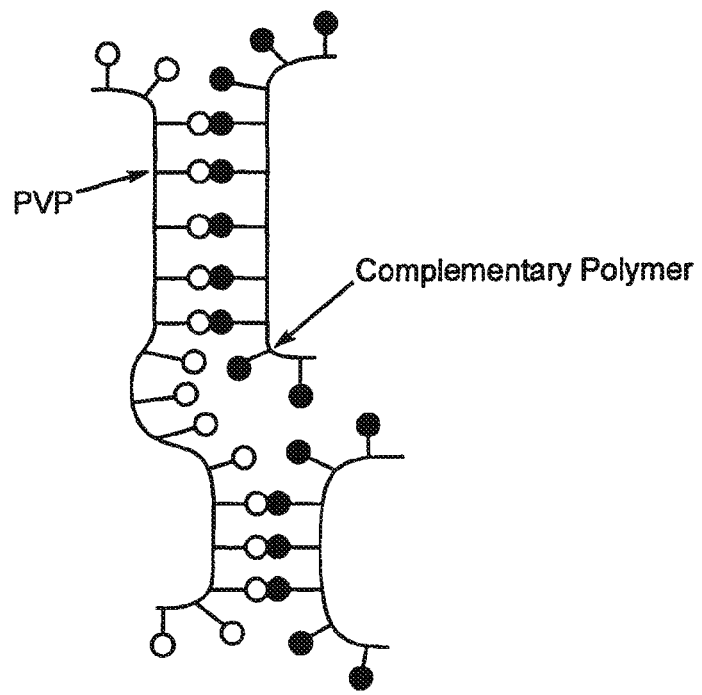
FIG. 2 is a schematic representation of a ladder-like PVP complex with a complementary proton-donating polymer as the ladder-like non-covalent crosslinker. When the complementary polymer contains reactive functional groups in repeating units of the backbone, the resulting complex has a so-called "ladder-like" structure.

The PVP-PEG complex combines high cohesive toughness (due to PVP-PEG H-bonding) with a large free volume (resulting from considerable length and flexibility of PEG chains). In order to emphasize enhanced free volume in the PVP-PEG blend, this type of complex structure is defined as a "carcass-like" structure (see FIG. 1). The carcass-like structure of the complex, results from the location of reactive functional groups at both ends of PEG short chains. When the ladder-like non-covalent crosslinker contains reactive functional groups in repeating units of the backbone, the resulting complex has so-called "ladder-like" structure (see FIG. 2). The ladder-like type of interpolymeric complexes were first described by Kabanov et al. (1979) Vysokomol. Soed. 21(A): 243-281). While the formation of the carcass-like complex leads to enhanced cohesive strength and free volume (which determines the adhesive properties of PVP-PEG blends), the formation of the ladder-like complex shown in FIG. 2 is accompanied by the loss of blend solubility and the increase of cohesive strength coupled with the decrease in free volume. For this reason, the structure of the ladder-like complex provides no adhesion.

Due to the decrease in free volume and the increase in cohesive energy, the PVP-PEG blend mixed with a long chain polymer giving the ladder-like complex with PVP, provides no or negligible initial tack. However, as the non-adhesive PVP-PEG blend with the long chain polymer is plasticized by water, the glass transition temperature of the blend shifts toward lower values, which are typical features of pressure-sensitive adhesives, and adhesion arises.

There are certain preferred combinations of components in the adhesive composition. For example, when the film-forming polymer is a poly(N-vinyl lactam) such as poly(N-vinyl pyrrolidone) or poly(N-vinyl caprolactam), the ladder-like crosslinker is preferably a polyacrylic acid, polymethacrylic acid, polymaleic acid, polyvinyl alcohol, poly(hydroxyalkyl acrylate), poly(hydroxyalkyl methacrylate) such as poly(hydroxyethyl methacrylate), methacrylic acid copolymer, or any other carboxyl-containing Eudragit.

Similarly, when the film-forming polymer is a poly(dialkyl aminoalkyl acrylate) or poly(dialkyl aminoalkyl methacrylate), then the ladder-like crosslinker is typically a hydroxyl containing polymer such as polyacrylic acid, polymethacrylic acid, or polymaleic acid. When the film-forming polymer is a polyvinyl alcohol, polyvinyl phenol, or poly (hydroxyalkyl acrylate) such as poly(hydroxyethyl methacrylate), the ladder-like crosslinker is preferably a poly(N-vinyl lactam) such as poly(N-vinyl pyrrolidone) or poly(N-vinyl caprolactam), as well as a homopolymer or copolymer of polyacrylic, polymethacrylic or polymaleic acid. When the film-forming polymer is polyethylene oxide, then appropriate ladder-like crosslinkers are polyacids such as homopolymers and copolymers of acrylic, methacrylic and maleic acids. Copolymers of poly(N-dialkylamino alkyl acrylate) with alkyl acrylate, methacrylate or ethacrylate monomers, a copolymer of poly(N-dialkylamino alkyl methacrylate) and alkyl acrylate, methacrylate or ethacrylate monomers can be used instead of the corresponding homopolymers both as film-forming polymers or ladder-like crosslinkers.

For any of the aforementioned combinations, a preferred carcass-like crosslinker is an oligomeric alkylene glycol comprising about 1-20 alkylene oxide units in its chain such as polyethylene glycol, carboxyl-terminated oligomeric alkylene glycol such as carboxyl-terminated poly(ethylene glycol), or polyhydric alcohols.

Other examples of suitable blends are shown below:

| film-forming polymer | ladder-like crosslinker | carcass-like crosslinker |
|---|---|---|
| PVCap | Eudragit series L and S such as L 100 and L 100-55, PAA, PMA, PVA, polyvinyl phenol, and PolyHEMA | PEG and carboxyl terminated PEG |
| PNIPAM | Eudragit series L and S such as L 100, L 100-55, S 100, PAA, PMA, alginic acid, PVA, and PolyHEMA | PEG and carboxyl terminated PEG |
| PEO | Eudragit series L and S such as L 100, L 100-55, and S 100; PAA, PMA, alginic acid, Gantrez ES-225, Gantrez ES-425, polyvinyl phenol | Propylene glycol, Glycerol, PEG, PEG-diacid |
| PAA, PMA | Eudragit series E, L, R and S such as E-100* and L 100-55, and polyvinyl amine | PEG |
| Eudragit E-100* | PAA, PMA, Eudragit series L such as L 100 and L 100-55, and alginic acid | Carboxyl terminated PEG, carbonic di- and polyvalent acids** |

*Eudragit E-100 is a copolymer of 2-dimethylaminoethyl methacrylate, butyl methacrylate and methyl methacrylate 2:1:1, commercially available from Röhm Pharma Polymers
**As described in U.S. Pat. No. 6,576,712

To illustrate the approach used herein, a PVP-PEG-Eudragit blend was used as a typical example, although the approach is general and can be easily reproduced using other water-soluble, hydrophilic polymers.

The properties of adhesive polymer blends were evaluated and are set forth in the examples. The behavior of these polymer blends was found to be typical of covalently crosslinked polymers. However, in contrast to covalently crosslinked systems, the triple polymer blends combining the carcass-like and the ladder-like non-covalent crosslinkers can be easily prepared using a straightforward process, and, furthermore, provide film-forming properties that are unattainable using chemically crosslinked polymers.

Another exemplary composition comprises: a film-forming polymer selected from water-swellable water-insoluble polymers and water-soluble polymers; a ladder-like non-covalent crosslinker that contains complementary reactive functional groups in the repeating units of the backbone, and is capable of forming a ladder-like interpolymer complex with the film-forming polymer; and a carcass-like non-covalent crosslinker that contains complementary reactive functional groups at its ends, and is capable of forming a carcass-like complex with at least one of the film-forming polymer or the ladder-like non-covalent crosslinker. The amount of the film-forming polymer is greater than the amount of either of the crosslinkers.

III. Adhesive Compositions-Optional Components

The adhesive compositions of the present invention are useful in any number of additional contexts, wherein adhesion of a product to a body surface is called for or desirable. These applications include, for example, drug delivery systems; wound dressings; conductive hydrogels; pressure-relieving cushions for application to a foot including heel cushions, elbow pads, knee pads, shin pads, forearm pads, wrist pads, finger pads, corn pads, callus pads, blister pads, bunion pads, and toe pads, all of which can include active agents for the treatment of dicubitis, veinous and diabetic foot ulcers, and the like; intraoral applications such as teeth whitening strips, breath freshener films for treating halitosis, and oral care products to treat sore throat, mouth ulcer/canker sore, gingivitis, periodontal and oral infections, periodontal lesions, dental caries or decay, and other periodontal diseases; transmucosal applications; adhesives for affixing medical devices, diagnostic systems and other devices to be affixed to a body surface; sealants for ostomy devices, prostheses, and face masks; sound, vibration or impact absorbing materials; carriers in cosmetic and cosmeceutical gel products; as well as many other uses known to or readily ascertainable by those of ordinary skill in the art, or as yet undiscovered.

Depending upon the particular intended use, there are numerous components that can be incorporated in the composition or combined with the composition to form a medical patch, bandage or device. These are detailed below.

A. Active Agents

Any of the presently described compositions may be modified so as to contain an active agent, and thereby act as an active agent delivery system when applied to a body surface in active agent-transmitting relation thereto. The release of active agents loaded into the compositions typically involves both absorption of water and desorption of the agent via a swelling-controlled diffusion mechanism. Active agent-containing compositions may be employed, by way of example, in transdermal drug delivery systems, in wound dressings, in topical pharmaceutical formulations, in implanted drug delivery systems, in oral dosage forms, in teeth whitening strips, and the like.

Such agents would be present in a cosmeceutically or therapeutically effective amount. Suitable active agents that may be incorporated into the present compositions and delivered topically or systemically (e.g., with a transdermal, oral, or other dosage form suitable for systemic administration of a drug) include, but are not limited to: adrenergic agents; adrenocortical steroids; adrenocortical suppressants; alcohol deterrents; aldosterone antagonists; amino acids; ammonia detoxicants; anabolic agents; analeptic agents; analgesic agents; androgenic agents; anesthetic agents; anorectic compounds; anorexic agents; antagonists; anterior pituitary activators and anterior pituitary suppressants; anti-acne agents; anti-adrenergic agents; anti-allergic agents; anti-amebic agents; anti-androgen agents; anti-anemic agents; anti-anginal agents; anti-anxiety agents; anti-arthritic agents; anti-asthmatic agents and other respiratory drugs; anti-atherosclerotic agents; anti-bacterial agents; anti-cancer agents, including antineoplastic drugs, and anti-cancer supplementary potentiating agents; anticholinergics; anticholelithogenic agents; anti-coagulants; anti-coccidal agents; anti-convulsants; anti-depressants; anti-diabetic agents; anti-diarrheals; anti-diuretics; antidotes; anti-dyskinetics agents; anti-emetic agents; anti-epileptic agents; anti-estrogen agents; anti-fibrinolytic agents; anti-fungal agents; anti-glaucoma agents; antihelminthics; anti-hemophilic agents; anti-hemophilic Factor; anti-hemorrhagic agents; antihistamines; anti-hyperlipidemic agents; anti-hyperlipoproteinemic agents; antihypertensive agents; anti-hypotensives; anti-infective agents such as antibiotics and antiviral agents; anti-inflammatory agents, both steroidal and non-steroidal; anti-keratinizing agents; anti-malarial agents; antimicrobial agents; anti-migraine agents; anti-mitotic agents; anti-mycotic agents; antinauseants; antineoplastic agents; anti-neutropenic agents; anti-obsessional agents; anti-parasitic agents; antiparkinsonism drugs; anti-pneumocystic agents; anti-proliferative agents; anti-prostatic hypertrophy drugs; anti-protozoal agents; antipruritics; anti-psoriatic agents; antipsychotics; antipyretics; antispasmodics; anti-rheumatic agents; anti-schistosomal agents; anti-seborrheic agents; anti-spasmodic agents; anti-tartar and anti-calculus agents; anti-thrombotic agents; anti-tubercular agents; antitussive agents; anti-ulcerative agents; anti-urolithic agents; antiviral agents; anxiolytics; appetite suppressants; attention deficit disorder (ADD) and attention deficit hyperactivity disorder (ADHD) drugs; bacteriostatic and bactericidal agents; benign prostatic hyperplasia therapy agents; blood glucose regulators; bone resorption inhibitors; bronchodilators; carbonic anhydrase inhibitors; cardiovascular preparations including anti-anginal agents, anti-arrhythmic agents, beta-blockers, calcium channel blockers, cardiac depressants, cardiovascular agents, cardioprotectants, and cardiotonic agents; central nervous system (CNS) agents; central nervous system stimulants; choleretic agents; cholinergic agents; cholinergic agonists; cholinesterase deactivators; coccidiostat agents; cognition adjuvants and cognition enhancers; cough and cold preparations, including decongestants; depressants; diagnostic aids; diuretics; dopaminergic agents; ectoparasiticides; emetic agents; enzymes which inhibit the formation of plaque, calculus or dental caries; enzyme inhibitors; estrogens; fibrinolytic agents; fluoride anticavity/antidecay agents; free oxygen radical scavengers; gastrointestinal motility agents; genetic materials; glucocorticoids; gonad-stimulating principles; hair growth stimulants; hemostatic agents; herbal remedies; histamine H2 receptor antagonists; hormones; hormonolytics; hypnotics; hypocholesterolemic agents; hypoglycemic agents; hypolipidemic agents; hypotensive agents; HMGCoA reductase inhibitors; immunizing agents; immunomodulators; immunoregulators; immunostimulants; immunosuppressants; impotence therapy adjuncts; inhibitors; keratolytic agents; leukotriene inhibitors; LHRH agonists; liver disorder treatments; luteolysin agents; memory adjuvants; mental performance enhancers;

metal chelators such as ethylenediaminetetraacetic acid, tetrasodium salt; mitotic inhibitors; mood regulators; mucolytics; mucosal protective agents; muscle relaxants; mydriatic agents; narcotic antagonists; nasal decongestants; neuroleptic agents; neuromuscular blocking agents; neuroprotective agents; nicotine; NMDA antagonists; non-hormonal sterol derivatives; nutritional agents, such as vitamins, essential amino acids and fatty acids; ophthalmic drugs such as antiglaucoma agents; oxytocic agents; pain relieving agents; parasympatholytics; peptide drugs; plasminogen activators; platelet activating factor antagonists; platelet aggregation inhibitors; post-stroke and post-head trauma treatments; potentiators; progestins; prostaglandins; prostate growth inhibitors; proteolytic enzymes as wound cleansing agents; prothyrotropin agents; psychostimulants; psychotropic agents; radioactive agents; regulators; relaxants; repartitioning agents; scabicides; sclerosing agents; sedatives; sedative-hypnotic agents; selective adenosine A1 antagonists; serotonin antagonists; serotonin inhibitors; serotonin receptor antagonists; steroids, including progestogens, estrogens, corticosteroids, androgens and anabolic agents; smoking cessation agents; stimulants; suppressants; sympathomimetics; synergists; thyroid hormones; thyroid inhibitors; thyromimetic agents; tranquilizers; tooth desensitizing agents; tooth whitening agents such as peroxides, metal chlorites, perborates, percarbonates, peroxyacids, and combinations thereof; unstable angina agents; uricosuric agents; vasoconstrictors; vasodilators including general coronary, peripheral and cerebral; vulnerary agents; wound healing agents; xanthine oxidase inhibitors; and the like.

Specific active agents with which the present adhesive compositions are useful include, without limitation, anabasine, capsaicin, oxybutynin, isosorbide dinitrate, aminostigmine, nitroglycerine, verapamil, propranolol, silabolin, foridone, clonidine, cytisine, phenazepam, nifedipine, fluacizin, and salbutamol.

The composition can also include any cosmetically active agent. As used herein, a "cosmetically active agent" includes any substance that can be released from the composition to effect a desired change in the appearance of the skin, teeth or surrounding tissue, or which imparts a socially desirable characteristic to the user, such as fresh breath. For example, a cosmetically active agent can be a breath freshener or an agent which effects whitening or bleaching of the teeth. Recognizing that in some cultures or in certain segments of Western society coloration of the teeth may be significant or desirable, the cosmetically active agent can also be any agent which imparts a color or tint to the teeth.

B. Other Ingredients

The compositions made by the methods described herein, may also comprise conventional additives such as absorbent fillers, preservatives, pH regulators, plasticizers, softeners, thickeners, antioxidants, pigments, dyes, conductive species, refractive particles, stabilizers, toughening agents, tackifiers or adhesive agents, detackifiers, flavorants and sweeteners, antioxidants, and permeation enhancers. In those embodiments where adhesion is to be reduced or eliminated, conventional detackifying agents may be used. These additives, and the amounts thereof, are selected in such a way that they do not significantly interfere with the desired chemical and physical properties of the hydrogel composition.

Absorbent fillers may be advantageously incorporated to control the degree of hydration when the adhesive is on the skin or other body surface. Such fillers can include microcrystalline cellulose, talc, clay, lactose, guar gum, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, and woven, non-woven paper, and cotton materials. Other suitable fillers are inert, i.e., substantially non-adsorbent, and include, for example, polyethylenes, polypropylenes, polyurethane polyether amide copolymers, polyesters and polyester copolymers, nylon, and rayon. One preferred filler is colloidal silica, e.g., Cab-O-Sil® (available from Cabot Corporation, Boston Mass.).

Preservatives include, by way of example, p-chloro-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

Compounds useful as pH regulators include, but are not limited to, glycerol buffers, citrate buffers, borate buffers, phosphate buffers, and citric acid-phosphate buffers, which may be included so as to ensure that the pH of the composition is compatible with that of an individual's body surface. In addition, when the composition is to be applied to a tooth surface, the addition of a pH regulator can insure that the pH of the composition is compatible with that of the environment of the mouth and will not leach minerals from the surface of the teeth; in order to optimize whitening without demineralization of the teeth, calcium and/or fluoride salts can be included in the composition.

Suitable plasticizers and softeners include, by way of illustration and not limitation, alkyl and aryl phosphates such as tributyl phosphate, trioctyl phosphate, tricresyl phosphate, and triphenyl phosphate; alkyl citrate and citrate esters such as trimethyl citrate, triethyl citrate and acetyl triethyl citrate, tributyl citrate and acetyl tributyl citrate, acetyl triethyl citrate, and trihexyl citrate; alkyl glycerolates; alkyl glycolates; dialkyl adipates such as dioctyl adipate (DOA; also referred to as bis(2-ethylhexyl)adipate), diethyl adipate, di(2-methylethyl)adipate, and dihexyl adipate; dialkyl phthalates, dicycloalkyl phthalates, diaryl phthalates and mixed alkyl-aryl phthalates, including phthalic acid esters, as represented by dimethyl phthalate, diethyl phthalate, dipropyl phthalate, dibutyl phthalate, di(2-ethylhexyl)-phthalate, di-isopropyl phthalate, diamyl phthalate and dicapryl phthalate; dialkyl sebacates such as diethyl sebicate, dipropyl sebacate, dibutyl sebacate and dinonyl sebacate; dialkyl succinates such as diethyl succinate and dibutyl succinate; dialkyl tartrates such as diethyl tartrate and dibutyl tartrate; glycol esters and glycerol esters such as glycerol diacetate, glycerol triacetate (triacetin), glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate; hydrophilic surfactants, preferably hydrophilic non-ionic surfactants such as, for example, partial fatty acid esters of sugars, polyethylene glycol, fatty acid esters, polyethylene glycol fatty alcohol ethers, and polyethylene glycol sorbitan-fatty acid esters, as well as non-ionic surfactants such as ethylcellosolve; lower alcohols from ethyl to octyl; lower diols such as 1,2- and 1,3-propylene glycol; low molecular weight poly(alkylene oxides) such as polypropylene glycol and polyethylene glycol; polyhydric alcohols such as glycerol; sorbitol; tartaric acid esters such as dibutyl tartrate; and mixtures thereof.

Since the carcass-like non-covalent crosslinker may itself act as a plasticizer, it is not generally necessary to incorporate an added plasticizer. However, inclusion of an additional low molecular weight plasticizer in the composition may, in some cases, be advantageous. For example, both the adhesive and the water absorbing properties of the adhesive composition can be easily controlling by adding appropriate amounts of a plasticizer. The mechanism of plasticization results in the increase of free volume. By increasing the free volume, the plasticizer modifies the balance between cohesion energy and the free volume, which is a factor controlling the adhesion. Since the film-forming polymer, ladder-like crosslinker and carcass-like crosslinker are preferably hydrophilic materials, suitable plasticizers are also preferably hydrophilic in nature.

Preferred thickeners are naturally occurring compounds or derivatives thereof, and include, by way of example, collagen, galactomannans, starches, starch derivatives and hydrolysates, cellulose derivatives such as methyl cellulose, hydroxypropylcellulose, hydroxyethyl cellulose, and hydroxypropyl methyl cellulose, colloidal silicic acids, and sugars such as lactose, saccharose, fructose and glucose. Synthetic thickeners such as polyvinyl alcohol, vinylpyrrolidone-vinylacetate-copolymers, polyethylene glycols, and polypropylene glycols, may also be used.

Pigments and dyes of the type commonly used with a food, drugs, or cosmetics in connection with the human body, especially color additives permitted for use in foods which are classified as "certifiable" or "exempt from certification," can be used to color the composition. These colorizing compounds can be derived from natural sources such as vegetables, minerals or animals, or can be man-made counterparts of natural derivatives.

Colorizing compounds presently certified under the Food Drug & Cosmetic Act for use in food and ingested drugs include dyes such as FD&C Red No. 3 (sodium salt of tetraiodofluorescein); Food Red 17 (disodium salt of 6-hydroxy-5-{(2-methoxy-5-methyl-4-sulphophenyl)azo}-2-naphthalenesulfonic acid); Food Yellow 13 (sodium salt of a mixture of the mono and disulfonic acids of quinophthalone or 2-(2-quinolyl)indanedione); FD&C Yellow No. 5 (sodium salt of 4-p-sulfophenylazo-1-p-sulfophenyl-5-hydroxypyrazole-3 carboxylic acid); FD&C Yellow No. 6 (sodium salt of p-sulfophenylazo-B-napthol-6-monosulfonate); FD&C Green No. 3 (disodium salt of 4-{[4-(N-ethyl-p-sulfobenzylamino)-phenyl]-(4-hydroxy-2-sulfonium-phenyl)-methylene})-[1-(N-ethyl-N-p-sulfobenzyl)-3,5-cyclohexadienimine]); FD&C Blue No. 1 (disodium salt of dibenzyldiethyldiaminotriphenylcarbinol trisulfonic acid anhydrite); FD&C Blue No. 2 (sodium salt of disulfonic acid of indigotin); FD&C Red No. 40; Orange B; and Citrus Red No. 2; and combinations thereof in various proportions.

Colorizing compounds exempt from FDA certification include annatto extract; beta-apo-8'-carotenal; beta-carotene; beet powder; canthaxanthin; caramel color; carrot oil; cochineal extract (carmine); toasted, partially defatted, cooked cottonseed flour; ferrous gluconate; fruit juice; grape color extract; grape skin extract (enocianina); paprika; paprika oleoresin; riboflavin; saffron; turmeric; turmeric oleoresin; vegetable juice; and combinations thereof in various proportions.

The form of the colorizing compound for use in the composition preferably includes dye form additives, but may also include lake forms which are compatible with the materials used in the hydrogel compositions. Water soluble dyes, provided in the form of powders, granules, liquids or other special-purpose forms, can be used in accordance with the present method. Preferably, the "lake", or water insoluble form of the dye, is used. For example, if a suspension of a colorizing compound is to be used, a lake form additive can be employed. Suitable water insoluble dye lakes prepared by extending calcium or aluminum salts of FD&C dyes on alumina include FD&C Green #1 lake, FD&C Blue #2 lake, FD&C R&D #30 lake and FD&C # Yellow 15 lake.

Other suitable colorizing compounds include non-toxic, water insoluble inorganic pigments such as titanium dioxide; chromium oxide greens; ultramarine blues and pinks; and ferric oxides. Such pigments preferably have a particle size in the range of about 5 to about 1000 microns, more preferably about 250 to about 500 microns. The concentration of the colorizing compound in the composition is preferably from about 0.05 to 10 wt %, and is more preferably from about 0.1 to 5 wt %. More than one colorizing compound can be present so that multiple colors are imparted therein. These multiple colors can be patterned into stripes, dots, swirls, or any other design which a consumer may find pleasing. The colorizing compound can also be used with other appearance-enhancing substances such as glitter particles.

The compositions can be rendered electrically conductive for use with biomedical electrodes and in other electrotherapy contexts, i.e., to attach an electrode or other electrically conductive member to the body surface, by the inclusion of conductive species. For example, the composition, formulated so as to exhibit pressure-sensitive adhesion, may be used to attach a transcutaneous nerve stimulation electrode, an electrosurgical return electrode, or an EKG electrode to a patient's skin or mucosal tissue. These applications involve modification of the hydrogel composition so as to enhance conductivity and contain a conductive species. In order to enhance conductivity, adding of poly-2-acrylamido-2-methyl propane sulfonic acid or its use as the film-forming polymer or the ladder-like crosslinker can be helpful. Suitable conductive species are ionically conductive electrolytes, particularly those that are normally used in the manufacture of conductive adhesives used for application to the skin or other body surface, and include ionizable inorganic salts, organic compounds, or combinations thereof. Examples of ionically conductive electrolytes include, but are not limited to, ammonium sulfate, ammonium acetate, monoethanolamine acetate, diethanolamine acetate, sodium lactate, sodium citrate, magnesium acetate, magnesium sulfate, sodium acetate, calcium chloride, magnesium chloride, calcium sulfate, lithium chloride, lithium perchlorate, sodium citrate, sodium chloride, and potassium chloride, and redox couples such as a mixture of ferric and ferrous salts such as sulfates and gluconates. Preferred salts are potassium chloride, sodium chloride, magnesium sulfate, and magnesium acetate, and potassium chloride is most preferred for EKG applications. Although virtually any amount of electrolyte may be present in the adhesive compositions of the current invention, typically the electrolyte is present at a concentration in the range of about 0.1-15 wt % of the composition.

Refractive particles are particles that refract and reflect light striking the adhesive and the color of the reflected light changes as the angle at which the composition is viewed is changed. Exemplary refractive particles are those made from embossed, aluminized polyester.

Suitable stabilizers include, parabens such as methyl paraben and propyl paraben.

Tackifiers or adhesive agents can also be included to improve the adhesive and tack properties of the composition, which is particularly beneficial to maintain adhesiveness when the composition is used in a manner such that it is subjected to a large amount of mechanical stress. The mechanism underlying tack improvement results from the large size and hydrophobic character of tackifier molecules. When mixed with interpolymer complex composition, the tackifier can increase the free volume causing only a slight impact upon the energy of cohesion. Suitable tackifiers may be solid or liquid. Exemplary materials include tacky rubbers such as polyisobutylene, polybutadiene, butyl rubber, polystyrene-isoprene copolymers, polystyrene-butadiene copolymers, and neoprene (polychloroprene). Preferred adhesive agents include low molecular weight polyisobutylene and butyl rubber. Other examples of suitable tackifiers herein are those that are conventionally used with pressure sensitive adhesives, e.g., rosins, rosin esters (for example Sylvagum® RE 85K (formerly Zonester® 85K Resin) available from Arizona Chemical), polyterpenes, and hydrogenated aromatic resins in which a very substantial portion, if not all, of the benzene rings are converted to cyclohexane rings (for example, the Regalrez family of resins manufactured by Hercules, such as Regalrez 1018, 1033, 1065, 1078 and 1126, and Regalite R-100, the Arkon family of resins from Arakawa Chemical, such as Arkon P-85, P-100, P-115 and P-125) and hydrogenated polycyclic resins (typically dicyclopentadiene resins, such as Escorez 5300, 5320, 5340 and 5380 manufactured by Exxon Chemical Co.).

In those embodiments wherein adhesion is to be reduced or eliminated, conventional detackifying agents may also be used. Suitable detackifiers include, crosslinked poly vinyl pyrrolidone, silica gel, bentonites, and so forth.

For compositions that are to be used in the oral cavity, any natural or synthetic flavorant or food additive, such as those described in Chemicals Used in Food Processing, Pub. No. 1274, National Academy of Sciences, pages 63-258 (the entire disclosure of which is herein incorporated by reference) can be included in the compositions of the invention. Suitable flavorants include wintergreen, peppermint, spearmint, menthol, fruit flavors, vanilla, cinnamon, spices, flavor oils and oleoresins, as known in the art, as well as combinations thereof. The amount of flavorant employed is normally a matter of preference, subject to such factors as flavor type, individual flavor, and strength desired. Preferably, the composition comprises from about 0.1-5 wt % flavorant. Sweeteners'can also be included, such as sucrose, fructose, aspartame, xylitol and saccharine. Preferably, the composition comprises sweeteners in an amount from about 0.001-5.0 wt %.

Heat, light, impurities, and other factors can all result in oxidation of the hydrogel composition. Thus, antioxidants can be included in the composition to protect against light-induced oxidation, chemically induced-oxidation, and thermally-induced oxidative degradation during processing and/or storage. Oxidative degradation, as will be appreciated by those in the art, involves generation of peroxy radicals, which in turn react with organic materials to form hydroperoxides. Primary antioxidants are peroxy free radical scavengers, while secondary antioxidants induce decomposition of hydroperoxides, and thus protect a material from degradation by hydroperoxides. Most primary antioxidants are sterically hindered phenols, and preferred such compounds for use herein are tetrakis [methylene (3,5-di-tert-butyl-4-hydroxyhydrocinnamate)]methane (e.g., Irganox® 1010 available from Ciba-Geigy Corp., Hawthorne, N.Y.) and 1,3,5-trimethyl-2,4,6-tris[3,5-di-t-butyl-4-hydroxy-benzyl]benzene (e.g., Ethanox® 330 available from Ethyl Corp.). A particularly preferred secondary antioxidant that may replace or supplement a primary antioxidant is tris(2,4-di-tert-butylphenyl)phosphite (e.g., Irgafos® 168 available from Ciba-Geigy Corp.). Other antioxidants; including but not limited to multifunctional antioxidants, are also useful. Multifunctional antioxidants serve as both a primary and a secondary antioxidant. Irganox® 1520 D, manufactured by Ciba-Geigy is one example of a multifunctional antioxidant. Vitamin E antioxidants, such as that sold by Ciba-Geigy as Irganox® E17, are also useful in the present compositions. Other suitable antioxidants include, without limitation, ascorbic acid, ascorbic palmitate, tocopherol acetate, propyl gallate, butylhydroxyanisole (BHA), butylated hydroxytoluene (BHT), bis(1,2,2,6, 6-pentamethyl-4-piperidinyl)-(3,5-di-tert-butyl-4-hydroxybenzyl)butylpropanedioate, (available as Tinuvin® 144 from Ciba-Geigy Corp.) and a combination of octadecyl 3,5-di-tert-butyl-4-hydroxyhydrocinnamate (also known as octadecyl 3-(3',5'-di-tert-butyl-4'-hydroxyphenyl)propionate) (Naugard® 76 available from Uniroyal Chemical Co., Middlebury, Conn.) and bis(1,2,2,6,6-pentamethyl-4-piperidinylsebacate) (Tinuvin® 765 available from Ciba-Geigy Corp.). Preferably, the antioxidant is present in an amount up to about 2 wt % of the hydrogel composition; typically, the amount of antioxidant is in the range of about 0.05 wt % to 1.5 wt %.

One or more permeation enhancers can be included in the compositions described herein. With some active agents, it may be desirable to administer the agent along with a suitable permeation enhancer in order to achieve a therapeutically effective flux through the skin or mucosa. Selection of suitable permeation enhancers will depend upon the agent being delivered, as well as the enhancer's compatibility with the other components of the composition.

Exemplary permeation enhancers include, by way of illustration and not limitation, sulfoxides such as dimethylsulfoxide (DMSO) and decylmethylsulfoxide ($C_{10}MSO$); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween® (20, 40, 60, 80) and lecithin (U.S. Pat. No. 4,783,450 to Fawzi et al.); the 1-substituted azacycloheptan-2-ones, particularly 1-n-dodecylcyclazacycloheptan-2-one (Azone® available from Nelson Research & Development Co., Irvine, Calif.; see U.S. Pat. No. 4,557,934 to Cooper, and U.S. Pat. Nos. 3,989,816, 4,316,893, and 4,405,616 to Rajadhyaksha); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343 to Leeper et al.); amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid; and mixtures thereof.

A substrate can also be affixed to the composition. The substrate can be any surface that the composition is adhered to during manufacture, and can be a permanent substrate (e.g., a backing member) or a temporary substrate (e.g., a manufacturing tool or equipment surface or a release liner). Exemplary substrates include flexible, resilient materials such as fabric, and open-cell foams such as polyurethane, polystyrene, and polyethylene foams; polyesters; polyethylene; polypropylene; polyurethanes; polyether amides; and non-polymeric materials such as waxes (e.g., microcrystalline or paraffin waxes) a or wax/foam laminate. The substrate is typically in the range of about 15 microns to about 250 microns in thickness. The substrate can also be embedded or decorated with decorative items such as beads, rhinestones, or the like, as long as these items do not interfere with the visco-elastic properties of the substrate required for proper deformation of the composition onto the body surface. The substrate can also display letters, words, or images designed to be pleasing or attractive to a consumer. The substrate can also be translucent so that the composition is unobtrusive when worn. However, the substrate or the composition can optionally be colored, so that the composition is easily seen when worn. Preferably, if coloring is desired, the color will be present in the substrate. For example, the substrate can be colored with bright or vibrant colors which a consumer may find pleasing. The substrate can therefore comprise a colorizing compound, such as, for example, a dye, pigment or substance that can impart color when added to the material forming the substrate.

The composition may also be attached to a release liner, which is a disposable element that serves to protect the system prior to application. The release liner should be formed from a material impermeable to any active agents, as well as the composition itself, and that is easily stripped from the adhesive composition. Release liners are typically treated with silicone or fluorocarbons, and are commonly made from polyesters and polyethylene terephthalate.

The compositions of the invention are also suitable for use in a delivery system or patch, for example a transdermal drug delivery device. Exemplary systems would contain a drug reservoir, an outwardly facing backing layer, and a means for affixing the system to a body surface. In manufacturing such systems, the composition may be cast or extruded onto a backing layer or release liner, and serves as the skin-contacting face of the system. The composition may also be used as an active agent reservoir within the interior of such a system, with a conventional skin contact adhesive laminated thereto to affix the system to a patient's body surface.

Systems for the topical, transdermal, or transmucosal administration of an active agent typically may contain on of more of the following: a reservoir containing an effective amount of an active agent; an adhesive means for maintaining the system in active agent transmitting relationship to a body surface; a backing layer; a rate-controlling membrane; and a disposable release liner that covers the otherwise exposed adhesive, protecting the adhesive surface during storage and prior to use. In many such devices, the reservoir can also serve as the adhesive means, and the compositions of the invention can be used as the reservoir and/or the adhesive means.

IV. Methods of Making

The properties of the composition of the invention are readily controlled by adjusting one or more parameters during fabrication. For example, the adhesive strength of the composition can be controlled during manufacture in order to increase, decrease, or eliminate adhesion. This can be accomplished by varying type and/or amount of different components, or by changing the mode of manufacture. Also, with respect to the fabrication process, compositions prepared using a conventional melt extrusion process have generally, although not necessarily, somewhat different performance properties than compositions prepared using a solution cast technique. Furthermore, the degree to which the composition will swell upon contact with water can be varied by material selection. The compositions may vary in appearance from clear, transparent to translucent to opaque. In addition, certain compositions may be rendered translucent by changing the relative quantities of the components, or by changing the fabrication method (translucent hydrogels are more readily obtained using solution casting than melt extrusion). In this manner, the translucent composition allows the user to observe the therapeutic (wound healing) or cosmetic (e.g., whitening) process while it is occurring and determine when the desired effect has been obtained.

The compositions described herein are generally melt extrudable, and thus may be prepared using a simple blending and extruding process. The components of the composition are weighed out and then admixed, for example using a Brabender or Baker Perkins Blender, generally although not necessarily at an elevated temperature, e.g., about 90 to 170° C., typically 100 to 140° C. Solvents or water may be added if desired. The resulting composition can be extruded using a single or twin extruder, or pelletized. Alternatively, the individual components can be melted one at a time, and then mixed prior to extrusion. The composition can be extruded to a desired thickness directly onto a suitable substrate or backing member. The composition can be also extruded first, and then be pressed against a backing member or laminated to a backing member. A releasable liner may also be included. The thickness of the resulting film, for most purposes, will be in the range of about 0.050 to 0.80 mm, more usually in the range of about 0.37 to 0.47 mm.

Alternatively, the compositions may be prepared by solution casting, by admixing the components in a suitable solvent, e.g., a volatile solvent such as ethyl acetate, or lower alkanols (e.g., ethanol, isopropyl alcohol, etc.) are particularly preferred, at a concentration typically in the range of about 35 to 60% w/v. The solution is cast onto a substrate, backing member or releasable liner, as above. Both admixture and casting are preferably carried out at ambient temperature. The material coated with the film is then baked at a temperature in the range of about 80 to 100° C., optimally about 90° C., for time period in the range of about one to four hours, optimally about two hours. Accordingly, one embodiment of the invention is a method for preparing a composition of the invention, which involves the following steps: preparing a solution of the components in a solvent; depositing a layer of the solution on a substrate to provide a coating thereon; and heating the coated substrate to a temperature in the range of about 80 to 100° C. for a time period in the range of about 1 to 4 hours, thereby providing an adhesive composition on a substrate.

Thus, one embodiment of the invention is a method of manufacturing an adhesive composition. First, the materials are selected, then mixed to form an adhesive composition by melt extrusion or solution casting. Material selection is as described above. A film-forming polymer is selected first. Then, a ladder-like non-covalent crosslinker is selected that (1) contains complementary reactive functional groups in the repeating units of the backbone, and (2) is capable of forming a ladder-like interpolymer complex with the film-forming polymer selected. Finally, a carcass-like non-covalent crosslinker is selected that (1) contains complementary reactive functional groups at its ends, and (2) is capable of forming a carcass-like complex with at least one of the film-forming polymer selected or the ladder-like non-covalent crosslinker selected; and wherein the amount of the film-forming polymer is greater than the amount of the ladder-like non-covalent crosslinker or the amount of the carcass-like non-covalent crosslinker.

When tacky compositions are desired, solution casting is the preferred process. For preparation of substantially non-tacky compositions, melt extrusion is preferred. Either melt extrusion or solution casting techniques can be used to prepare translucent compositions, although solution casting is typically preferred for these embodiments.

Active agents can be added to the film-forming polymer, ladder-like non-covalent crosslinker, and carcass-like non-covalent crosslinker components, as they are all being mixed together. The active agent can be added as a solid or as a solution to the composition dissolved in solvent. The mixture is then cast as usual onto a suitable substrate and allowed to dry, although a lower drying temperature is desired when using this method of loading. Compositions prepared in this manner can be dried at ambient temperature for a time period ranging from about 1 hour to several days.

Alternately, the active agent can be added after the components are mixed and the composition prepared. One method of loading the composition with the active agent comprises layering a desired active agent, e.g., a tooth whitening agent, in aqueous solution onto the surface of the composition placed on a suitable substrate, or to place the active agent directly on the substrate. The release liner is then assembled on top of the composition, forming a sandwich structure, and the solution containing the active agent is absorbed into the composition due to its water-swellable properties. Thus, one embodiment of the invention is a method of forming a drug-containing composition, which involves the following steps: melt processing the components through an extruder to form an extruded composition; extruding the composition as a film of desired thickness onto a suitable erodible backing member; and, when cooled, and loading the film with an aqueous solution of the active agent, e.g., a peroxide. Alternatively, the composition layered onto the substrate can be submerged in a solution containing the desired concentration of active agent, and the solution absorbed into the composition. By measuring the rate of weight gain on absorbing the liquid, the percent loading of the composition with the active agent can be determined and controlled.

The invention also contemplates having a multiple layer system. For example, it may be desirable to include additional active agents that may not be compatible with the primary active agent during storage. In this manner, one layer can be the primary active agent-containing layer and the other layer(s) can contain additional actives. These other layers can be made of the composition of the invention, or any other biocompatible formulation known in the art (e.g., polyisobutylene, dimethyl siloxane, ethylene vinyl acetate, polyvinylacetate, cellulose acetate, butyrate, propionate, ethyl cellulose and water insoluble acrylates). In addition, depending on ordering of the layers, it may be desired to have a tacky layer, e.g., the layer to be positioned directly on the body surface, and a non-tacky layer, e.g., the outer layer that is positioned nearest the clothing or other area where contact is not desired. Another advantage of having a multiple layer system is that the ratio of polymers used in the outermost layer can be varied to achieve a non-tacky layers so as to avoid having to include a separate backing layer in the product.

A typical film thickness is from about 0.050 to 0.80 mm, preferably 0.25 to 0.50 mm. The thickness of the film is not critical, and can be varied according to the desired concentration of any active agent incorporated into the film, the length of time the composition is to be adhered to the body surface, the level of comfort desired by the wearer, and so forth.

V. Methods of Use

In practice, the compositions can be used simply by removing the product from its package, removing a release liner (when included) and applying the composition to the desired body surface, e.g., applied to the teeth that it is desired to whiten or placed on any body surface for use as a wound dressing or drug delivery system. The composition of the invention can be provided in a variety of sizes and configurations.

A backing member can be included, and may be formulated to be occlusive or impermeable to the active agent so as to reduce or prevent leakage of the active agent, from the composition, while the user wears the composition for the desired amount of time, i.e., the composition will then deliver the drug uni-directionally, e.g., only towards the body surface to which it is attached, such as the mucosal tissue. Alternately, the backing member can be formulated to have a predetermined permeability so as to provide for bi-directional drug delivery, e.g., towards the mucosal surface as well as towards the surrounding environment of the oral cavity. The level of permeability, i.e., its selective nature, can also be used to control the relative rates of delivery towards the attachment surface and the surrounding environment.

The composition can be maintained in the desired location for as little time as a few minutes, several hours, all day or overnight, and then removed when the desired therapeutic or cosmetic effect has been achieved. Alternately, when placed in a moist environment such as to oral cavity, the composition can be left in place and allowed to erode entirely. Accordingly, in one embodiment of the invention, a method for whitening teeth may simply comprise applying the composition, to teeth in need of whitening, while in another embodiment, the method may further comprise removing the composition when the desired degree of whitening has been achieved.

If desired, a translucent composition can be provided, and is worn without being obtrusive or noticeable to others. The system can also be designed without an active ingredient and finds utility as a protective dressing for an oral surface, e.g., as a wound dressing.

The composition can be worn for an extended period of time, but will typically be worn for a predetermined period of time of from about 10 minutes to about 24 hours, after which the composition can be removed or will have eroded away. For tooth whitening applications, a preferred time period is from about 10 minutes to about 8 hours (e.g., overnight), with 30 minutes to about 1 hour also being a preferred embodiment. For other active agents, a therapeutically or cosmeceutically effective time can be readily determined based upon the active agent that is being used as well as the condition being treated.

In one embodiment, the composition is a solid and is attached to the backing member during manufacture. Accordingly, the composition is applied in a single step. Alternately, the composition can be a non-solid and manufactured and packaged separate from the backing member. In that instance, the composition is first applied by the user, followed by the user applying the backing member to the outer surface of the composition. In either embodiment, the user can form the composition on the body surface, e.g., around the upper or lower teeth or other oral tissue, by applying normal manual pressure to the backing member with the tips of the fingers and thumbs, optionally by slightly moistening the composition or the body surface prior to application. Assuming the surface area of the average adult finger or thumb tip is approximately one square centimeter, the normal pressure generated by the finger and thumb tips is about 100,000 to about 150,000 Pascals (i.e., about 3 lbs. or 1.36 kg) per square centimeter. The pressure is typically applied to the composition by each finger and thumb tip for about one or two seconds. Once the pressure applied to the backing member by the tips of the fingers and thumbs is removed, the composition remains in the shape of, and adherent to, the body surface onto which it was formed.

When the user is ready to remove the composition, the composition can be removed simply by peeling it away from the body surface. If desired, the composition can be re-adhered for additional treatment time. Any residue left behind is minimal, and can be removed using conventional washing, tooth or oral cavity cleansing methods.

In one embodiment of the invention, the composition is a solid and is a pressure sensitive adhesive and absorbs water.

The composition can also be applied as a non-solid composition, for example applied as a liquid or gel. For example, the user can extrude the composition from a tube onto a finger for application to the teeth or other body surface, extrude the composition from a tube directly onto the teeth, apply the composition by means of a brush or other applicator, and so forth. The erodible backing member can then be applied as separate step after the liquid or gel is applied. After the evaporation of solvent, the liquid or gel composition dries to form a matrix-type polymer film or gel on the body surface. In one embodiment of this liquid or gel film-former composition, the composition contains sufficient water or other solvent to provide flowable property. In another embodiment of this composition, the polymer components of the liquid or gel composition are soluble in a water-ethanol mixture both at ambient temperature and at refrigeration temperatures of about 4° C., and are miscible upon solvent evaporation. In yet another embodiment of this liquid or gel film-former composition, the polymeric composition has a Lower Critical Solution Temperature of about 36° C. in an ethanol-water mixture. For use in the oral cavity, the resulting film (after solvent evaporation) is preferably insoluble or slowly soluble in saliva at body temperature so as to provide long lasting contact between the composition and the dental enamel.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in degrees Celsius (° C.), and pressure is at or near atmospheric.

Abbreviations

DMAEMA 2-dimethylaminoethyl methacrylate
Eudragit E 100 methacrylic acid copolymer, (Rohm America Inc.)
Eudragit L 100 methacrylic acid copolymer (Rohm America Inc.)
Eudragit L 100-55 methacrylic acid copolymer (Rohm America Inc.)
Eudragit S 100 methacrylic acid copolymer (Rohm America Inc.)
Gantrez S-97 maleic acid-methylvinyl ether copolymer (Internitional Specialty Products)
HPC hydroxypropylcellulose, MW=1,150,000
HPMCP hydroxypropylmethylcellulose phthalate
PEO polyethylene oxide, MW=200,000 g/mol
PG 1,2-propylene glycol
PVA Poly(vinyl alcohol), MW=75,000
PVP 90 Kollidon® 90F polyvinylpyrrolidone (BASF)
PEG 400 polyethylene glycol 400
TBC tributyl citrate
TEC triethyl citrate Example 1

Preparation and Properties of Adhesive Compositions Based on the Combination of the Ladder-Like and Carcass-Like Types of Crosslinking of the Film-Forming Polymer First, PVP 90 is selected as the film-forming polymer. In this case, examples of complementary polymers that are able to crosslink the PVP non-covalently by the formation of a water-insoluble ladder-like interpolymeric complex with PVP are: homopolymers or copolymers of polyacrylic acid (PAA), polymethacrylic acid (PMA), homopolymers or copolymers of maleic acid, homopolymers or copolymers of polyvinyl alcohol (PVA), homopolymers or copolymers of polyvinyl phenol, alginic acid and hydroxypropyl cellulose (HPC). One such non-covalent crosslinker of PVP is a copolymer of methacrylic acid and ethyl acrylate (1:1), commercially available from Röhm Pharma Polymers as Eudragit L 100-55. Blending the Eudragit L 100-55 with an adhesive PVP 90-PEG 400 mixture, results in the formation of an insoluble, homogeneous single-phase mixture. Being insoluble in water, the triple PVP-PEG-Eudragit blend was characterized in terms of Sol Fraction (%) and Swell Ratio, as shown in the table below and in FIGS. 4 and 5).

Preparation of the films: 50 g of PEG 400 was dissolved in 200 g of ethanol. Under vigorous stirring, the Eudragit L 100-55 powder was added in the amounts indicated below. Under vigorous stirring, the PVP 90 powder was added in amounts as indicated below. The mixture was stirred over 2 hours to obtain a homogeneous solution. The solution was stored over 2-5 hours to let air bubbles dissipate. Polymer films were prepared by solution casting onto a PET backing, followed by drying at ambient temperature over 3 days. Films of 0.20±0.03 mm were obtained. The water content in the obtained films was measured gravimetrically by weight loss at 120° C. The water content in the films was found to be in the range 11±1.5 wt %.

|  | Composition (grams) | | | Swell Ratio, g/g, pH = 4.6 | Sol Fraction, %, pH = 4.6 | Sol Swell Ratio, g/g, pH = 5.6 | Fraction, %, pH = 5.6 |
| --- | --- | --- | --- | --- | --- | --- | --- |
| Sample | PVP 90 | Eudragit L 100-55 | PEG 400 | | | | |
| 1-1 | 46 | 4 | 50 | 45.1 | 60.9 | 60.4 | 60.2 |
| 1-2 | 41.67 | 8.33 | 50 | 19.0 | 57.0 | 28.1 | 58.5 |
| 1-3 | 38.46 | 11.54 | 50 | 14.5 | 58.5 | 20.7 | 59.6 |
| 1-4 | 35.71 | 14.29 | 50 | 9.9 | 59.5 | 14.3 | 59.7 |
| 1-5 | 14.29 | 35.71 | 50 | 2.3 | 52.4 | 2.6 | 43.1 |

The swelling properties of the films were tested gravimetrically. The samples were placed into a 0.1 M buffer solution, at least 200-fold amount of solution was taken with respect to the sample weight. The samples were stored over 3 days at 25° C. The swollen samples were then accurately removed and dried at 110° C. The Swell Ratio and Sol Fraction were calculated as follows: Swell Ratio=$m_d/m_s$; Sol Fraction, %=$100 \cdot (m_0-m_d)/m_0$, where $m_0$ is initial sample weight, $m_s$ is the weight of the swollen sample and $m_d$ is the weight of the sample after drying.

Figure 4:
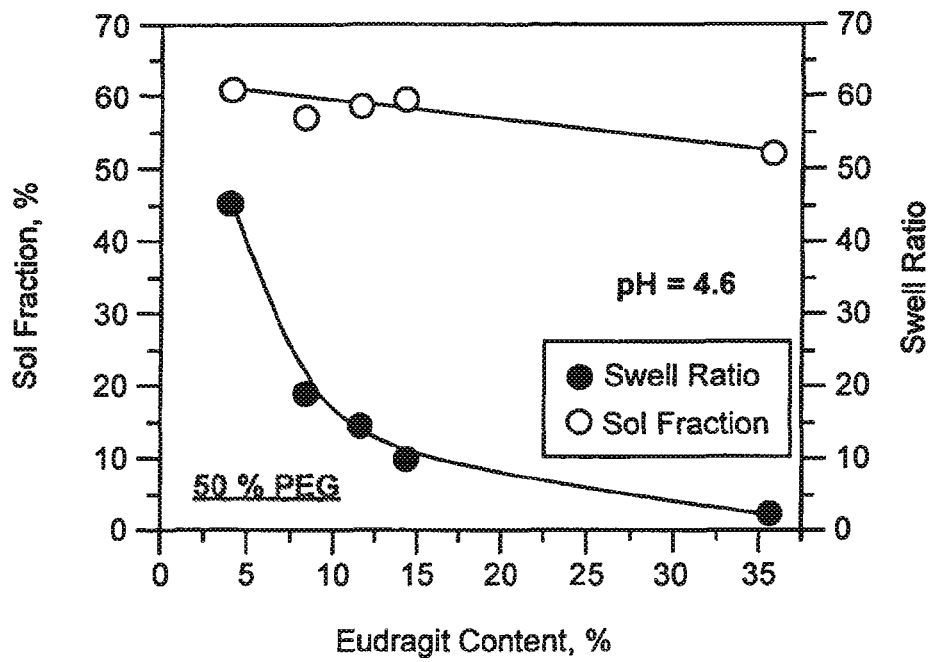
FIG. 4 demonstrates Sol Fraction and Swell Ratio (at a pH of 4.6) for the triple blends of PVP (50 wt %) with PEG and Eudragit L 100-55 as a function of the concentration of H-bonding, ladder-like crosslinker, Eudragit L 100-55.

According to the data shown above, the higher the pH in water, the greater the swell ratio, whereas the fraction of soluble blend was only slightly affected by pH. The higher the pH, the greater the degree of ionization of Eudragit carboxyl groups and the higher the swelling of the ladder-like complex in water. This data implies that the solubility of the blend in water (expressed in terms of sol fraction) is controlled by non-covalent crosslinking with the Eudragit and depends on the crosslinker content. Actually, with the increase of Eudragit concentration, the sol fraction decreased correspondingly (FIG. 4). The value of sol fraction was close to the content of PEG 400 in blends (FIG. 5), while the PVP was mainly in an insoluble state due to the ladder-like crosslinking with Eudragit.

Figure 5:
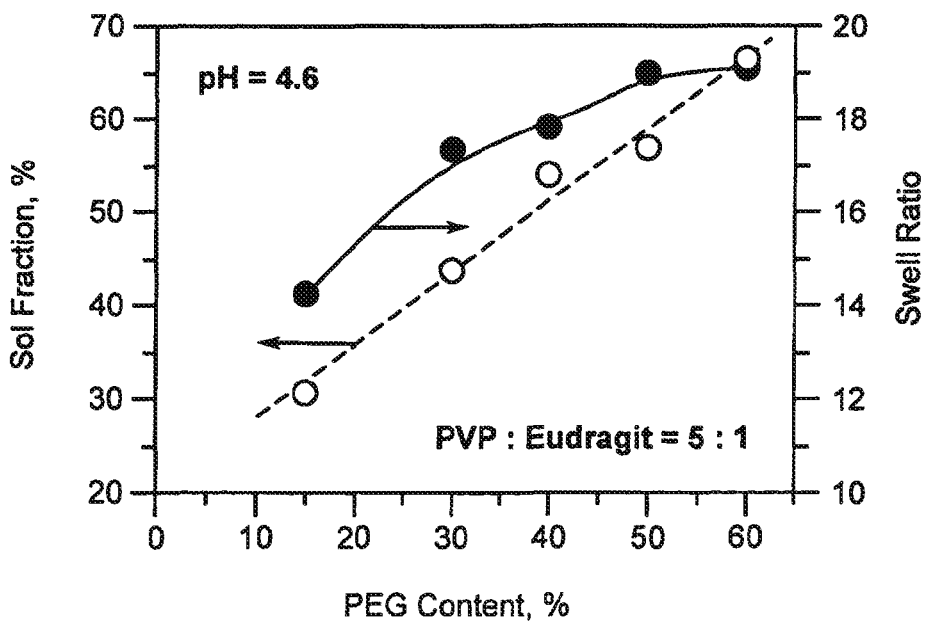
FIG. 5 shows the dependence of Sol Fraction and Swell Ratio (at a pH of 4.6) for the triple blends of PVP with PEG and Eudragit L 100-55 (PVP:Eudragit ratio of 5:1) to the concentration of H-bonding, carcass-like crosslinker, PEG.

Swell ratio is a measure of the degree of non-covalent crosslinking of the film-forming polymer (PVP). The higher the concentration of the ladder-like crosslinker, Eudragit L 100-55, the lower the swell ratio and the denser the network of PVP-Eudragit hydrogen bonds (FIG. 4). The carcass-like crosslinker, PEG, caused the increase of both swell ratio and sol fraction (FIG. 5). By this way, the swelling and dissolution of PVP-PEG-Eudragit triple blends can be readily changed by the change in blend composition.

Figure 6:
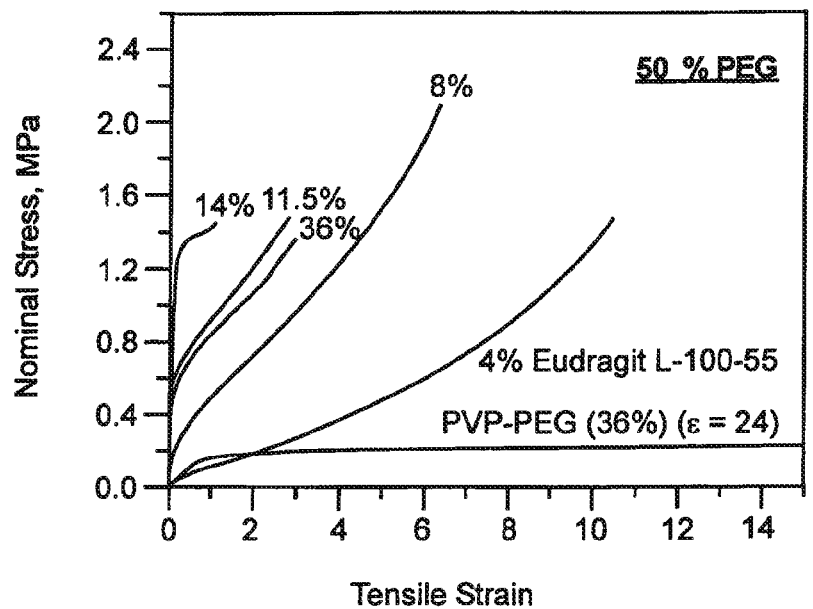
FIG. 6 demonstrates the effect of non-covalent, ladder-like crosslinker, Eudragit L 100-55, on tensile stress-strain curves up to break the films of PVP-PEG-Eudragit L 100-55 blends under uniaxial extension with drawing rate of 20 mm/min. The concentration of the carcass-like crosslinker PEG was fixed at 50 wt %.
Figure 7:
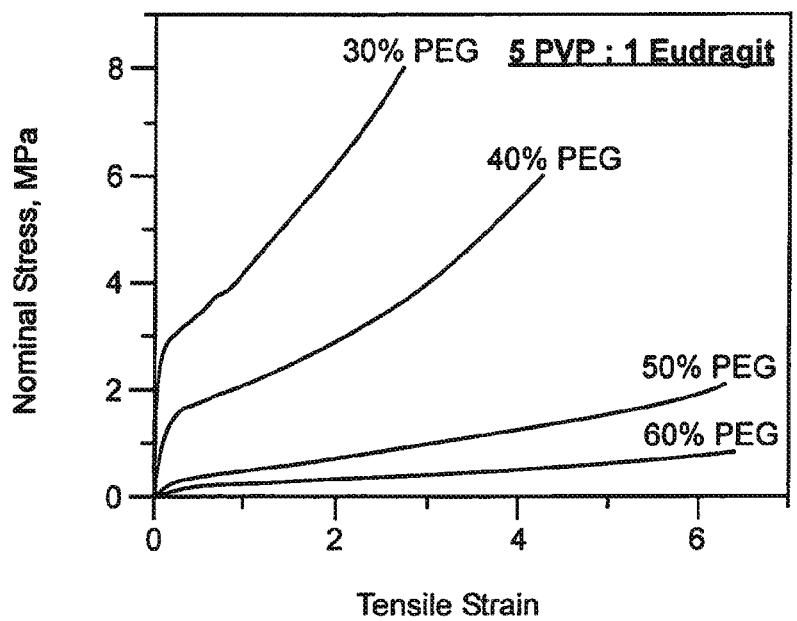
FIG. 7 illustrates the effect of the non-covalent, carcass-like crosslinker, PEG, on stress-strain curves up to break the films of PVP-PEG-Eudragit L 100-55 blends under uniaxial extension with drawing rate of 20 mm/min. The PVP:Eudragit L 100-55 ratio is 5:1.

Varying the ratio of film-forming polymer (PVP 90) to the ladder-like crosslinker (Eudragit L 100-55) and the content of the carcass-like crosslinker (PEG 400), was found to be a feasible tool to control the mechanical properties of adhesive hydrogels. Tensile properties of the PVP-PEG-Eudragit hydrogels were typical of those for cured rubbers (FIG. 6). Adding the ladder-like non-covalent crosslinker, Eudragit, to the PVP-PEG adhesives described in U.S. Pat. No. 6,576,712 to Feldstein et al., caused a sharp gain in mechanical strength and the loss of ductility. The ultimate tensile stress came through a maximum at 8% Eudragit content, while the maximum elongation at break decreased smoothly with the rise of the Eudragit concentration for single-phase blends. Two-phase compositions exemplified by 36% Eudragit blend exhibited a slight increase of ductility, accompanied with the loss of cohesive strength. The carcass-like crosslinker, PEG, was a good plasticizer for the PVP-PEG-Eudragit triple blends. The rise in PEG content promoted the ductility of hydrogel films (FIG. 7).

Example 2

Adhesive Properties of Hydrogels in Swollen State

This example demonstrates the adhesive properties of the PVP-PEG-Eudragit L 100-55 blend as function of hydration degree. Preparation of films: 30 g of PEG 400 was dissolved in 280 g of ethanol. Under vigorous stirring, 12 g of Eudragit L 100-55 powder was added. Under vigorous stirring, 58 g of PVP 90 powder was added. The mixture was stirred over 2 hours to obtain a homogeneous solution. The solution was stored over 5 hours to let air bubbles dissipate. Polymer films were prepared by solution casting onto a PET backing, followed by drying at ambient temperature over 1 day. The films then were dried in an oven at 110° C. overnight. Films of a size of 0.20±0.04 mm were obtained. The PVP-PEG-Eudragit L 100-55 films of different hydration degree were prepared by spraying controlled amounts of distilled water over film surfaces. The films then were covered with a PET release liner, sealed in aluminum pouches and stored over 7 days to insure uniform distribution of water within the film samples. Water content in the obtained films was measured gravimetrically by weight loss at 120° C. Films with a hydration degree ranging from 11 to 40 wt % and higher were prepared as indicated in the table below. The adhesive properties of hydrated PVP-PEG-Eudragit films (FIG. 8-10) were tested in accordance with ASTM D 2979 method using a TAXT2 Texture Analyzer Machine. A stainless steel probe with average roughness 50 nm was used, a contact pressure was 0.8 MPa, contact time was 1 sec, debonding rate was 0.1 mm/sec.

| Water Content, % | $W_{debonding}$, J/m$^2$ | Maximum stress, MPa |
|---|---|---|
| 11% | 1 | 0.12 |
| 15% | 14 | 0.46 |
| 17% | 16 | 0.44 |
| 20% | 10 | 0.24 |
| 30% | 9 | 0.20 |
| 35% | 10 | 0.17 |
| 40% | 11 | 0.15 |

Figure 8:
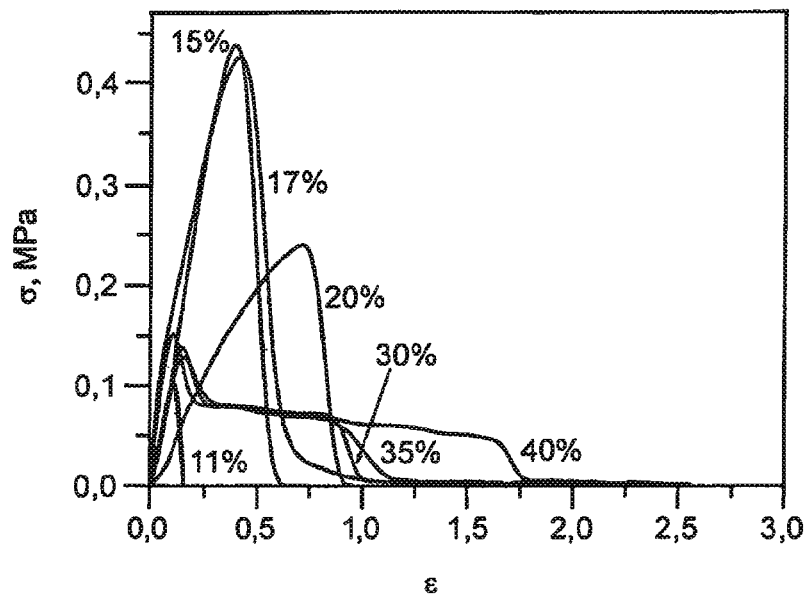
FIG. 8 illustrates the impact of absorbed water upon adhesive properties of the PVP-PEG-Eudragit L 100-55 blends, where the composition contains 58 wt % PVP, 30 wt % PEG, and 12 wt % of the Eudragit L 100-55. The amounts of absorbed water (in wt %) are indicated.
Figure 9:
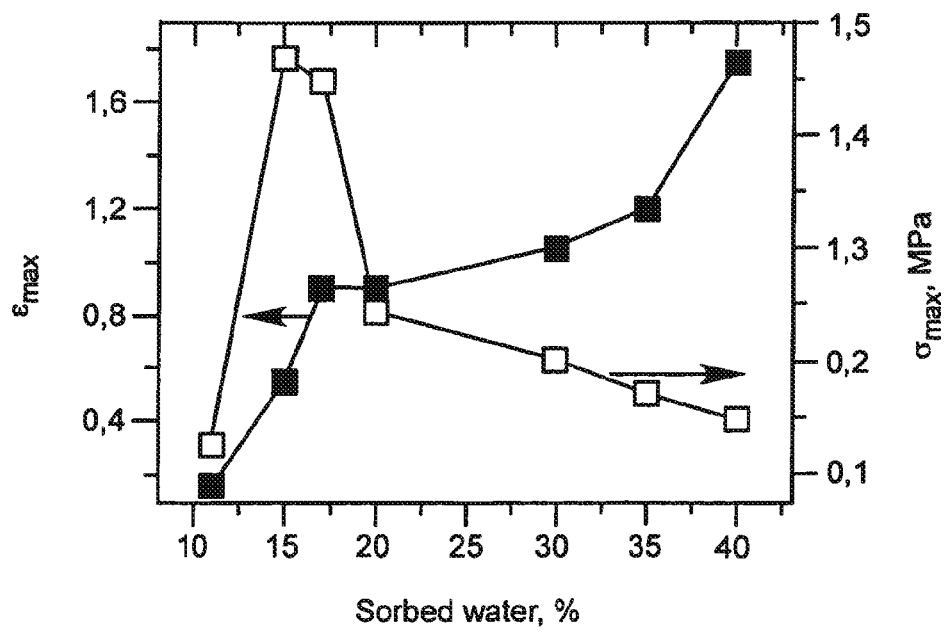
FIG. 9 is a plot of the maximum stress and maximum of elongation under adhesive debonding versus the weight fraction of absorbed water for the PVP-PEG-Eudragit L 100-55 hydrogel.
Figure 10:
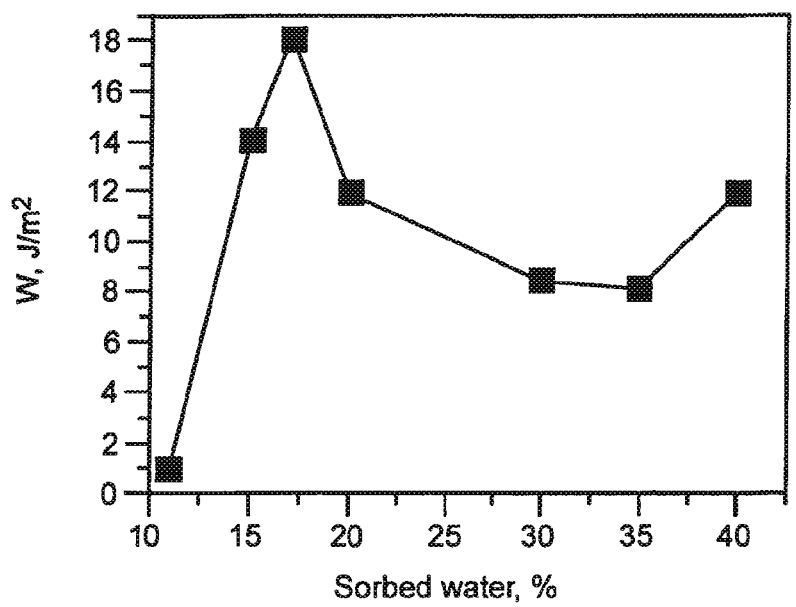
FIG. 10 displays the work of adhesive debonding as a function of absorbed water for PVP-PEG-Eudragit L 100-55 hydrogel.

The value of maximum stress in probe tack stress-strain curves is traditionally considered as a measure of tack. The maximum tack was documented at approximately 15-17% hydration degree (FIGS. 8 and 9). However, the more accurate measure of adhesion is the total amount of energy dissipated in the course of debonding process (the work of debonding). The work of debonding is shown in FIG. 10 as the function of water content in swollen hydrogel. As follows from the data in FIG. 10, the adhesion towards probe was high enough even at 40% hydration degree. At comparatively low degrees of hydration of the blend, the type of adhesive bond failure was always adhesive. As the content of absorbed water exceeded 50%, the type of debonding became cohesive. In this way, the PVP-PEG/Eudragit L 100-55 (12%) blends revealed the properties that are typical of both pressure sensitive adhesives (high adhesion) and bioadhesives (enhancement of adhesion in the course of swelling in water). Such unique coupling the high adhesion with the capability to increase a tack under hydration has never been earlier reported.

Example 3

Effect of Composition of Methacrylic Acid Copolymers on Performance Properties of their Blends with a PVP-PEG Adhesive In the following example PVP 90 was chosen as the film-forming polymer, whereas copolymers of methylmethacrylate and methacrylic acid (Eudragit L 100 and Eudragit S 100) served as the ladder-like crosslinkers. PEG 400 was used as the carcass-like crosslinker. Films were prepared and tested.

Eudragit L 100 differs from Eudragit L 100-55 by the composition of hydrophobic monomer, while the content of monomer units of methacrylic acid is the same (50%). In Eudragit L 100-55 the hydrophobic monomer units are represented by ethyl acrylate, while Eudragit L 100 is a copolymer of methacrylic acid with methyl methacrylate. In turn, Eudragit S 100 is distinguished from Eudragit L 100 by the decreased content of the units of methacrylic acid (33% instead of 50%), whereas methyl methacrylate is hydrophobic monomer in both copolymers.

Preparation of films: 40 g of PEG 400 was dissolved in 280 g of a water/ethanol (1:1) mixture. The required amount of sodium hydroxide was dissolved (as indicated in the table below). Under vigorous stirring, 12 g of Eudragit L 100-55 powder was added. Under vigorous stirring, 58 g of PVP 90 powder was added. The mixture was stirred over 2 hours to obtain a homogeneous solution. The solution was stored over 5 hours to let air bubbles dissipate. Polymer films were prepared by solution casting onto a PET backing, followed by drying at ambient temperature over 3 days. Films of 0.20±0.04 mm thickness were obtained. Water content in the films was measured gravimetrically by weight loss at 120° C. Films with a hydration degree of 10±1.5 wt % were obtained.

The adhesive properties of these PVP-PEG-Eudragit films are set forth below:

| Sample | PVP 90, g | PEG 400, g | Eudragit L 100, g | Eudragit S 100, g | NaOH, g | $W_{debonding}$, J/m² | Maximum stress, MPa |
|---|---|---|---|---|---|---|---|
| 4-1 | 60 | 40 | 10 | 0 | 0.108 | 9 | 0.26 |
| 4-2 | 60 | 40 | 0 | 10 | 0.054 | 11 | 0.37 |

The PVP-PEG blends with Eudragit L 100 as the ladder-like crosslinker were found to be soluble in water, while the blends containing Eudragit S 100 as the ladder-like crosslinker were water swellable hydrogels.

Example 4

Compositions Containing Methacrylic Acid Copolymers as the Film-Forming Polymer and PVP as the Ladder-Like Crosslinker While in the Examples 1-3, the film-forming polymer was PVP and the ladder-like crosslinker was either Eudragit L 100-55, L 100, or S 100, this example represents an inverted composition, where the Eudragit serves as the film-forming polymer and the ladder-like crosslinker is PVP. Sol fraction corresponded closely to the content of water-soluble carcass-like crosslinker, PEG, indicating that the formation of the ladder-like interpolymer complex resulted in an insoluble product.

| Composition of Example 4, wt. % | | | | |
|---|---|---|---|---|
| Eudragit L 100-55 | PVP 90 | PEG 400 | Sol Fraction, % | Swell Ratio |
| 50 | 10 | 40 | 44.9 | 2.03 |

In this way, by varying the composition of PVP-PEG-Eudragit L 100-55 blends, adhesive materials of various degrees of hydrophilicity were obtained, where the values of the swell ratio ranged between 2 to 60.

Example 5

Gradually Dissolving and Swellable Adhesive Blends of PVP-PEG Carcass-Like Complex with Non-Acrylic Carboxyl-Containing Ladder-Like Crosslinkers PVP 90 was selected as the film-forming polymer and PEG 400 was selected as carcass-like crosslinker and enhancer of adhesion. Copolymers of maleic acid and cellulose derivatives bearing carboxyl groups were then evaluated and determined to be suitable ladder-like crosslinkers.

One of most illustrative examples of using the copolymers of maleic acid with methylvinyl ether as the ladder-like crosslinker in PVP-PEG complex is provided by the Gantrez S-97 copolymer. PVP blends containing 40 wt % of PEG and 5, 10 and 15 wt % of Gantrez were obtained by casting/drying in water-ethanol solutions (1:1). All the blends were soluble in water, although the time required for full dissolution of the films was in linear relationship to the content of the ladder-like crosslinker (Gantrez). In contrast, the less Gantrez content in the blends, the higher the adhesion.

Another typical example supporting the proposal that different carboxyl-containing polymers are suitable ladder-like crosslinkers of electron-donating hydrophilic polymers such as PVP is provided by HPMCP. PEG 400 was used as the carcass-like crosslinker of PVP 90.

Preparation of films: 40 g of PEG 400 was dissolved in 240 g of ethanol/water mixture (80 wt parts ethanol:20 wt parts water). Then under vigorous stirring, the required amounts of HPMCP and PVP were dissolved. The mixture was stirred over 2 hours to obtain a homogeneous solution. The solution was stored over 5 hours to let air bubbles dissipate. Polymer films were prepared by solution casting onto a PET backing, followed by drying at ambient temperature over 3 days. Films of 0.20±0.04 mm thickness were obtained. The adhesive behavior of these swollen hydrogels followed the pattern exhibited by PVP-PEG-Eudragit L 100-55 blends. Swelling and dissolution properties of the films are presented below.

| Sample | PVP 90, g | PEG 400, g | HPMCP, g | Swell Ratio, g/g | Sol Fraction, % |
|---|---|---|---|---|---|
| 5-1 | 50 | 40 | 10 | 48.3 | 85.3 |
| 5-2 | 45 | 40 | 15 | 30.5 | 71.0 |

Example 6

Using Hydroxyl-Containing Hydrophilic Polymers as the Ladder-Like Crosslinkers of PVP in Adhesive Hydrogels The list of appropriate ladder-like crosslinkers of the electron-donating hydrophilic film-forming polymers, exemplified here by PVP, is not exhausted by polyacids. Other suitable hydrophilic polymers bear hydroxyl group in their repeating units. This example demonstrates the suitability of PVA and hydroxyl-containing cellulose derivatives such as HPC as ladder-like crosslinkers of PVP.

Blends of PVP 90 with PVA, with PEG, PG or glycerol as the carcass-linker crosslinker, can be prepared as follows. Under vigorous stirring, the required amount Of PVA was dissolved in distilled water at 95° C. (9 wt parts of water was taken to dissolve 1 wt part of PVA). Then under vigorous stirring, the required amounts of PG and PVP were dissolved. The mixture was stirred over 2 hours at 85° C. to obtain a homogeneous solution. Polymer films were prepared by solution casting onto a backing member, following by drying at ambient temperature over 3 days. Films of 0.20±0.02 mm thickness were obtained. The adhesive properties of the films were found to be similar to those observed with PVP-PEG-Eudragit L 100-55 blends. The results of sol-gel analysis are listed below.

| Sample | PVP 90, g | PVA, g | PG, g | Swell Ratio, g/g | Sol Fraction, % |
|---|---|---|---|---|---|
| 6-1 | 50 | 10 | 40 | 35.0 | 74.0 |
| 6-2 | 45 | 15 | 40 | 26.0 | 69.0 |
| 6-3 | 40 | 20 | 40 | 14.6 | 66.0 |
| 6-4 | 35 | 25 | 40 | 14.0 | 61.5 |

Another appropriate ladder-like crosslinker of PVP is HPC. High molecular weight PVP 90 (58.67 wt %), PEG 400 (29.33%) and HPC were dissolved in ethyl alcohol under stirring. The resulting solution was cast onto a release liner and dried at 50° C. An alternative method of blend production involves direct mixing of the components followed by mixture extrusion as indicated below in Example 11. The prepared blend possessed a soluble fraction of 62% and swell ratio of 10.13. The adhesive behavior of the formulation follows the pattern shown by PVP-PEG-Eudragit L 100-55 blends.

An adhesive blend containing 58.67 wt % of PVP 90, 29.33 wt % of PEG 400, 9.6 wt % of HPC and 2.4 wt % of Eudragit L 100-55 was prepared as indicated above. The properties of this composition were found to be intermediate between those of PVP-PEG-Eudragit L 100-55 and PVP-PEG-HPC blends. The content of sol fraction was 48% and swell ratio was 6.8.

Example 7

PVP-Free Adhesive Hydrogels Based on the Interpolymer Complexes Involving the Combination of the Ladder-Like and Carcass-Like Crosslinking Although PVP is one of most successful representatives of the hydrophilic polymers suitable to serve as film-forming components in the adhesives of the invention, others appropriate film-forming polymers include PEO. PEO is a much weaker electron donating polymer as compared to PVP. For this reason, the PEO is capable of forming sufficiently strong hydrogen bonds with strong proton-donating polymers such as polyacids.

A blend containing 68.2 wt % of PEO, 25 wt % of PG as the carcass-like crosslinker and 6.8 wt % of Gantrez S-97 as the ladder-like crosslinker, was prepared by casting/drying of a water solution. The prepared film of 0.2 mm in thickness was cohesively tough (ultimate tensile stress was 5.0 MPa) indicating that the PEO is crosslinked due to H-bonding with the carboxyl groups of Gantrez S-97. Upon film immersion into water, the film dissolved over 1-2 minutes. Appreciable tack was observed for moderately hydrated films. The maximum tack (about 0.8 MPa) was observed with the film containing 13 wt % of water.

Example 8

Preparation and Properties of Adhesive Compositions Based on the Ladder-Like Interpolymer Complexes While the hydrophilic adhesives presented above are formed due to hydrogen bonding between polymeric components, the samples shown in the table below, illustrate the properties of hydrogels prepared by coupling the H-bond and electrostatic crosslinking of the film-forming polymer. Electrostatic interactions, as a rule, are stronger than H-bonding. Eudragit E-100 was used as the film-forming polymer, which is a copolymer of DMAEMA, butyl methacrylate and methyl methacrylate (2:1:1). The monomer units of DMAEMA are capable of forming electrostatic bonds with carboxyl groups in the ladder-like crosslinker, Eudragit L 100-55.

| | Blend composition, wt % | | | | |
|---|---|---|---|---|---|
| Sample | Eudragit E-100 | Eudragit L 100-55 | PEG 400 | Sol Fraction, % | Swell Ratio |
| 8-1 | 68 | 7 | 25 | 25.5 | 2.75 |

Example 9

Performance Properties of Adhesive Compositions Based on Interpolymer Complexes Compared to Conventional Pressure Sensitive Adhesives and Bioadhesives The properties of the triple blend hydrogels of the invention (PVP-PEG-Eudragit L 100-55), were compared with those of: conventional pressure sensitive adhesives (PSA; DURO-TAK® 34-4230, National Starch and Chemicals); classical bioadhesives (covalently crosslinked polyacrylic acid polymers Carbopol® 974P and Noveon® AA1, both from B.F. Goodrich, Co.); PVP-PEG binary blends, described in U.S. Pat. No. 6,576,712 to Feldstein et al.; and the hydrophilic adhesives of the invention (Examples 1-7)

| Attribute | PSA | Bioadhesive | PVP-PEG | Hydrophilic |
|---|---|---|---|---|
| Peel adhesion, N/m | | | | |
| in dry state | 300-600 | None | 50-70 | 10-30 |
| in hydrated state | None | 10-60 | 300-550 | 100-300 |
| Solubility in water | Insoluble | Insoluble, Swellable | Soluble | Insoluble, Swellable |
| Water sorption capacity | Less 1% | 98% | Non limited | 96% |
| Film-forming capability | Yes | No | Yes | Yes |
| Elastic modulus, Pa × $10^5$ | 1.0-5.0 | 0.09-0.9 | 1.3-5.0 | 0.4-40 |
| Maximum elongation | 22 | More than 30 | 22 | 2.7 |
| Ultimate tensile strength, MPa | 16 | 0.01 | 12 | 30.4 |
| Logarithm Yield stress, MPa | 4.1 | 2.6 | 3.7-4.9 | 5.0 |

PSAs, exemplified above by the SIS block-copolymer based DURO-TAK® 34-4230 adhesive, represent a special class of viscoelastic polymers. They are capable of forming a strong adhesive bond with various substrates under application of a slight external pressure over a short time (1-2 seconds). It is noteworthy that the typical PSAs for human use are mainly based on hydrophobic elastomers with low glass transition temperatures, ranging from −120 to −30° C., which are usually increased by addition of tackifying resins. The common property of the PSAs is a loss of adhesion as the surface of a substrate is moistened. For this reason, conventional PSAs cannot be used for application to highly hydrated and soft biological tissues such as oral mucosa. For this purpose, hydrophilic bioadhesives are usually employed, which are generally nontacky in the dry state, but adhere to wet substrates. The adhesive strength of such bioadhesives, however is usually much lower than that of the PSAs.

As is seen from this data, the adhesives of the present invention share properties of both pressure sensitive adhesives and bioadhesives. Indeed, while their adhesive strength was typical of the PSAs, they exhibited increased adhesion towards moistened substrate like bioadhesives. Varying the hydrogel composition can easily provide the further control of adhesive, water sorption and mechanical properties of the products based on non-covalently crosslinked hydrogels (See FIGS. 3-7).

The peel adhesion towards dry and moistened human forearm skin in vivo for conventional acrylic PSA and three grades of adhesives based on interpolymer complexes of the invention, was evaluated. The data established that the adhesive properties of the water-soluble PVP-PEG adhesives described in U.S. Pat. No. 6,576,712 share the properties of PSAs and bioadhesives by combining the high adhesion featured for conventional PSAs with the ability to adhere to moistened skin and biological tissues typical of bioadhesives. The adhesive behavior of the water-soluble PVP-PEG adhesives and the PVP-PEG-Eudragit L 100-55 adhesives of the invention were compared with the properties of two different grades of conventional PSAs: SIS-based DURO-TAK® 34-4230 PSA and acrylic PSA (3M).

Expressed in terms of maximum stress under debonding, the tack of adhesives based on the interpolymer complexes was found to be comparable with that of conventional PSAs. However, a distinctive feature of the adhesive blends of the invention was the lower values of maximum elongation that resulted from the non-covalent crosslinking of the chains of film-forming polymer. Because the carcass-like crosslinking is significantly looser than the ladder-like crosslinking, the water-soluble PVP-PEG adhesive demonstrated higher stretching at probe detachment than observed with adhesives having the ladder-like type of crosslinking. In this regard, it is pertinent to note that the main tools to increase fluidity and maximum elongation of the adhesives provided by the ladder-like crosslinking, is the dilution of network density due to mixing with carcass-like crosslinkers that can function as plasticizers, in the course of swelling in water and also the decrease in concentration of the ladder-like crosslinker.

Example 10

Preparation of Adhesive Films by Direct Mixing of Polymeric Components Followed by Extrusion The behavior of the hydrophilic and amphiphilic adhesives of the invention is typical of covalently crosslinked polymers. In contrast to covalently crosslinked systems, however, the adhesives based on interpolymer complexes can be easily prepared using a simpler blending process, and, furthermore, provide film-forming properties that are unattainable using crosslinked polymers.

While the formulations described in the examples above were prepared by casting from solutions followed by drying, the adhesive films of the invention can be also produced by direct mixing of the components in the dry state followed by extrusion. Direct mixing was done using a Thermo Haake Mixer, whereas the extrusion procedure was performed with a Skania Single-Screw Extruder. The procedures of mixing and extrusion are described below.

Preparation of a PVP-PEG-Eudragit Composition

The blend composition was as follows: 58.7 wt % PVP 90; 9.33 wt % PEG 400; and 12.0 wt % Eudragit L 100-55.

Mixing Procedure: The total amounts of PEG and Eudragit were mixed at room temperature. An amount of PVP was then added at room temperature to reach convenient consistency, producing a premix. This premix was loaded in the mixer under stirring at 30 rpm at 55° C. The remaining PVP was then introduced by small portions, with an increase in stirring intensity to 60 rpm. The mixing regime is presented below.

| Time, min. | $T_{mixture}$, ° C. | n, rpm | Torque, N-m | Operation |
|---|---|---|---|---|
| 0-4 | 54 | 30 | 4.2-5.7 | loading of premix |
| 12 | 55 | 30 | 11.0-12.5 | loading of remaining PVP |
| 24 | 65 | 60 | 14.0-16.0 | mixing |
| 34 | 75 | 0 | — | stop |

Extrusion Procedure: The die with the slit thickness of 100 μm and width of 6.5 cm was constructed to prepare the film with the thickness of ~5 mil. Two temperature regimes, I and II, were used, as shown below.

| Regime | $T_{zones}$ | $T_{roller}$ | N, rpm | Extrusion speed, mm/c | Reducing step | Pressure, Bar |
|---|---|---|---|---|---|---|
| I | 100/100/105 | 100 | 20 | 4.82 | 14 | 72 |
| II | 118/120/119 | 100 | 20 | 6.73 | 14 | 68 |

The formulation layer was then extruded (without any filter) between two PET anti-adhesion films and pull out with a linear speed of ~5-7 mm/c.

Preparation of a PVP-PEG-HPC Composition

The blend composition was as follows: 58.67 wt % PVP 90; 29.33 wt % PEG 400; and 12.0 wt % HPC. The mixing procedure was as described above, and the mixing regime is presented below.

| Time, min. | T mixture, ° C. | n, rpm | Torque, N-m | Operation |
|---|---|---|---|---|
| 0 | 54 | 30 | 0 | loading of premix |
| 12 | 58 | 30 | 4.4 | loading of remaining PVP |
| 22 | 59 | 30 | 8-9 | start of temperature elevation |
| 32 | 110 | 30 | 2-3 | introducing the HPC |
| 42 | 123 | 0 | — | stop |

The extrusion procedure was as described above, and the regime is presented below

| $T_{zones}$ | $T_{roller}$ | N, rpm | Extrusion speed, mm/c | Reducing step | Pressure, Bar |
|---|---|---|---|---|---|
| 120/120/130 | 100 | 15 | 7.29 | 14 | 56 |

Preparation of a PVP-PEG-HPC-Eudragit Composition

The blend composition was as follows: 58.67 wt % PVP 90; 29.33 wt % PEG 400; 9.60 wt % HPC; and 2.40 wt %

Eudragit L 100-55. The mixing and extrusion procedures were as described above, and the regimes are presented below.

| Time, min. | T mixture, °C. | n, rpm | Torque, N-m | Operation |
|---|---|---|---|---|
| 0 | 55 | 30 | 2.6 | loading of premix |
| 3 | 58 | 30 | 6.6 | loading of remaining PVP |
| 12 | 58 | 30 | 7 | start of temperature elevation |
| 25 | 115 | 30 | 1.4 | introducing the HPC |
| 36 | 120 | 30 | 3.5 | introducing the Eudragit |
| 55 | 119 | 0 | — | stop |

| $T_{zones}$ | $T_{roller}$ | N, rpm | Extrusion speed, mm/c | Reducing step | Pressure, Bar |
|---|---|---|---|---|---|
| 110/110/115 | 100 | 20 | 7.29 | 14 | 67 |

Example 11

Wound Dressings

The following samples illustrate how the hydrogel compositions of this invention may be used for silver-containing antimicrobial wound dressings. Wound dressing films were prepared from the following ingredients:

| | Composition (wt %) | | | |
|---|---|---|---|---|
| Sample | Film-forming polymer | Ladder-like crosslinker | Carcass-like crosslinker | Silver salt, 1.0 wt % |
| 11-1 | Eudragit L 100-55 (49.5) | PVP (9.9) | PEG 400 (39.6) | Silver sulfate |

The antimicrobial dressing was insoluble in water and exudate, but were swellable, thus absorbing a great amount of exudate. The dressing was initially tacky and maintained a good adhesion toward dry and moderately exudating wounds, but could be removed from the skin without pain by washing with a large amount of water. Accordingly, the dressing of this example is useful for treatment of pressure, diabetic, arterial and venous ulcers.

The potentiometric method with an Ag ion selective electrode was used to study silver release from the dressing. Aqueous solutions of silver nitrate in the concentration range $2.5 \times 10^{-6}$-$10^{-3}$ M were used to calibrate the Ag ion selective electrode. Circular samples (1" diameter; 5 cm² area) of the film was die-cut and laminated to glass plates by means of a double-sided tape. The glass plate with the Ag release side upwards was placed into a beaker and 50 ml of distilled water was poured into the beaker. The system was then covered with a petri-dish and placed into an oven, set to 25±0.2° C. After specified time points the receptor solution in the beaker over the sample was stirred and the silver concentration was measured with the Ag ion selective electrode. After measurement the receptor solution was removed and replaced with 50 ml of distilled water. Cumulative Ag release was calculated and expressed in μg per cm² of the anti-microbial dressing. Sample 11-1 was found to deliver a high amount of silver sulfate.

Example 12

Tooth Whitening Strips

One embodiment of a composition for tooth whitening was prepared from the following ingredients using a melt extrusion process:

| Component | Sample 12-1 (wt %) |
|---|---|
| PVP (Film-forming polymer) | 44 |
| Eudragit L 100-55 (Ladder-like crosslinker) | 9 |
| PEG (Carcass-like crosslinker) | 22 |
| Hydrogen peroxide | 6 |
| Water, stabilizers, pH regulators | 19 |
| Total | 100 |

The ingredients were melt processed in a Brabender single screw extruder as follows. The Eudragit L 100-55 was added to the extruder first, followed by PVP and PEG, at a temperature of 100 to 150° C. The composition was extruded to a thickness of 0.35 mm between two polyethylene terephthalate release liners. A hydrogen peroxide solution was added to the extruded film. Being applied to tooth surface, the initially nontacky film adhered immediately to tooth enamel, swelled and dissolved slowly in saliva, releasing the hydrogen peroxide.

Figure 11:
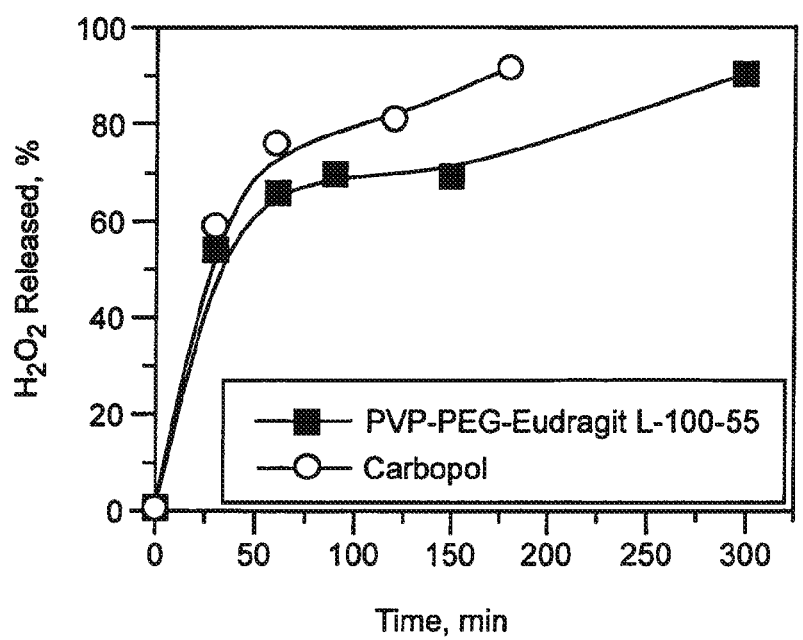
FIG. 11 illustrates the in vivo release profile of hydrogen peroxide from tooth whitening strips based on a Carbopol bioadhesive and on the PVP-PEG-Eudragit L 100-55 hydrogel.

FIG. 11 compares the in vivo release profiles of the hydrogen peroxide from a tooth whitening strip based on PVP-PEG-Eudragit L 100-55 composition and from Crest Whitestrips™ (Proctor & Gamble Co., Cincinnati, Ohio; referred to as the "Crest Product"). The Crest Product contained 5.3% hydrogen peroxide in a Carbopol 956 gel on a thin polyethylene film. The Carbopol is a classic representative of bioadhesive hydrogels made due to covalent crosslinking of polyacrylic acid. The amount of hydrogen peroxide released in vivo was measured by the remainder of hydrogen peroxide in the product removed from teeth surface upon a predetermined period of wearing. The composition of the present invention provided a prolonged hydrogen peroxide release compared to the Crest Product. Indeed as compared to the Carbopol-based matrix in the Crest Product, the bioadhesive PVP-PEG-Eudragit L 100-55 film in present invention provided a retarded the rate of dissolution. In turn, prolonged release of hydrogen peroxide from the composition of present invention provided improved the tooth whitening effect.

Example 13

Liquid Tooth Whitening Formulations

Adhesive blends described in this invention can be applied either in the form of adhesive films or as solutions in appropriate solvents, which are capable of forming the film upon, drying at application site. To prepare a liquid teeth whitener, the following components were mixed:

| Sample | Composition (wt %) | | | | | |
|---|---|---|---|---|---|---|
| | Film-forming polymer | Ladder-like crosslinker | Carcass-like crosslinker | Solvent | Active agent | pH regulator |
| 17-1 | PVP 90 (12.00) | Eudragit L 100-55 (0.75) | PEG 400 (3.00) | water (33.12) and ethanol (33.00) | carbamide peroxide (18.00) | sodium citrate (0.13) |
| 17-2 | PVP 90 (7.00) | Eudragit L 100-55 (4.00) | PEG 400 (1.00) | ethanol (35.00) | carbamide peroxide (18.00) | sodium citrate (0.13) |
| 17-3 | PVP K-30 (13.50) and PVP 90 (3.00) | Eudragit L 100-55 (7.20) and Eudragit RL (3.60) | PEG 400 (7.00) | water (15.00) and ethanol (40.50) | hydrogen peroxide (10.00) | sodium citrate (0.20) |

Eudragit RL is a copolymer of trimethylammonioethyl methacrylate chloride with ethylacrylate and methylmethacrylate (0.2:1:2), available from Röhm Pharma Polymers. Being insoluble in aqueous media, in the hydrogel composition, it serves to protect the hydrogel film from fast dissolution.

When applied to teeth surface and allowed to dry for 30 seconds, the liquid compositions form a thin hydrogel film, staying on the teeth for a period longer 30 minutes and provide a tooth whitening effect.

Example 14

Adhesive Matrices with Therapeutic Agents

The following compositions were prepared by dissolution in ethanol of components listed below, casting the solution and drying at temperature of 50° C.

The sample uses an acrylate polymer (Eudragit E 100) as the film-forming polymer. The Eudragit L-100-55 is the ladder-like crosslinker of Eudragit E 100, and PVP is the ladder-like crosslinker of the Eudragit L-100-55. PVP also helps to increase blend hydrophilicity. PEG is the carcass-like crosslinker of PVP. The sample also includes an alkyl citrate (TEC) as a plasticizer.

| Component | Sample 14-1 (wt %) |
|---|---|
| Eudragit E 100 | 58.29 |
| TEC | 26.10 |
| Eudragit L 100-55 | 2.61 |
| PVP 90 | 2.00 |
| PEG 400 | 1 |
| Lidocaine base | 10 |
| Total | 100 |

Example 15

Liquid Film-Forming Bandages

In this example, adhesives were formulated with a soluble ladder-like crosslinker, along with a ladder-like and carcass-like crosslinker for the soluble ladder-like crosslinker. The main component was an insoluble film-forming polymer, and a plasticizer was included.

Samples 15-1 to 15-4 represent liquid compositions suitable for application to skin as liquid bandages. Sample 15-1 is a liquid formulation for tooth whitening which contains the insoluble film-forming polymer (Eudragit RS) and plasticizer for this polymer tributylcitrate (TBC). Eudragit RS is a copolymer of trimethylammonioethylmethacrylate chloride (0.1) with ethylacrylate (1) and methylmethacrylate (2), available from Röhm Pharma Polymers. Samples 15-2 to 15-4 contain no ladder-like crosslinker for the PVP Ladder-like crosslinker.

Liquid bandage and cold sore compositions for skin applications may also contain active agents such as local anesthetics. Suitable local anesthetics include dibucaine hydrochloride; dibucaine; lidocaine hydrochloride; lidocaine; benzocaine; p-butylaminobenzoic acid 2-(diethylamino) ethyl ester hydrochloride; procaine hydrochloride; tetracaine hydrochloride; chloroprocaine hydrochloride; oxyprocaine hydrochloride; mepivacaine; cocaine hydrochloride; and piperocaine hydrochloride.

Any natural or synthetic flavorants, such as those described in Chemicals Used in Food Processing, Pub. No. 1274, National Academy of Sciences, pages 63-258, can be included in the compositions of the invention. Suitable flavorants include wintergreen, peppermint, spearmint, menthol, fruit flavors, vanilla, cinnamon, spices, flavor oils (oil of cloves) and oleoresins, as known in the art, as well as combinations thereof. The amount of flavorant employed is normally a matter of preference, subject to such factors as flavor type, individual flavor, and strength desired.

Sample 15-3 also contains a skin softening agent such as glycerol monooleate (Peceol, Gattefossé, France).

| Sample | Composition, wt % | | | | | | |
|---|---|---|---|---|---|---|---|
| | Film-forming polymer (A) | Plasticizer for (A) | Ladder-like crosslinker (B) | Ladder-like crosslinker for (B) | Carcass-like crosslinker for (B) | Additives | Solvent |
| 15-1 | Eudragit RS, 29.00 | TBC, 2.50 | PVP K-90, 3.00 | Eudragit L 100-55, 2.20 | PEG, 3.00 | Sodium Citrate, 2.50 | Ethanol, 38.20 |
| 15-2 | Eudragit RS, 35.11 | TBC, 11.70 | PVP K-90, 0.36 | — | PEG, 0.18 | — | Ethanol, 52.65 |

-continued

| Sample | Film-forming polymer (A) | Plasticizer for (A) | Ladder-like crosslinker (B) | Ladder-like crosslinker for (B) | Carcass-like crosslinker for (B) | Additives | Solvent |
|---|---|---|---|---|---|---|---|
| 15-3 | Eudragit RS, 20.06 | TBC, 6.69 | PVP K-90, 0.21 | — | PEG, 3.00; 1,2-Propylene Glycol, 28.57 | GMO, 14.29 | Ethanol, 30.09 |
| 15-4 | Eudragit RS, 7.95 | TBC, 4.55 | PVP K-17, 1.14 | — | PEG, 1.14 | — | Ethanol, 35.00 |

The practice of the present invention will employ, unless otherwise indicated, conventional techniques of polymer chemistry, adhesive manufacture, and hydrogel preparation, which are within the skill of the art. Such techniques are fully explained in the literature.

It is to be understood that while the invention has been described in conjunction with the preferred specific embodiments, the description and examples that are presented above are intended to illustrate and not limit the scope of the invention. Other aspects, advantages and modifications will be apparent to those skilled in the art to which the invention pertains. All patents, patent applications, journal articles, and other references cited herein are incorporated by reference in their entireties.

What is claimed is:

1. A method of preparing a bioadhesive, tooth whitening composition comprising:
   (i) blending a mixture comprising a (1:1) methyacrylic acid-ethyl acrylate copolymer, polyvinylpyrrolidone, poly(ethylene glycol) having a molecular weight from 200-600, and a tooth whitening agent, to thereby form a blended polymer-tooth whitening agent composition, wherein the amount of polyvinylpyrrolidone on a weight basis is greater than the amount of the methyacrylic acid-ethyl acrylate copolymer or the amount of the poly(ethylene)glycol,
   (ii). melting the blended polymer-tooth whitening agent composition from (i) to form a melted composition, and
   (iii). extruding the melted composition from (ii) to form an extruded tooth whitening composition,
   the extruded tooth whitening composition comprising from about 20-95 wt % polyvinylpyrrolidone, from about 0.5-40 wt % of methyacrylic acid-ethyl acrylate copolymer, and from about 0.5-60 wt % poly(ethylene glycol).

2. The method of claim 1 wherein the tooth whitening agent is selected from the group consisting of peroxides, metal chlorites, perborates, percarbonates, peroxyacids, and combinations thereof.

3. The method of claim 1, wherein in step (iii), the melted composition is extruded onto a suitable substrate or backing member.

4. The method of claim 1, wherein the extruded tooth whitening composition comprises about 30-50 wt % polyvinyl pyrrolidone; about 5-10 wt % (1:1) methyacrylic acid-ethyl acrylate copolymer; and about 15-30 wt % polyethylene glycol.

5. The method of claim 2, wherein the tooth whitening agent is hydrogen peroxide.

6. The method of claim 5, wherein the extruded tooth whitening composition comprises from about 5-25 wt % hydrogen peroxide.

7. The method of claim 1, wherein the melting step is carried out at a temperature from about 90° C. to 170° C.

8. The method of claim 7, wherein the melting step is carried out at a temperature from about 100° C. to 140° C.

9. The method of claim 1, wherein additional components are present in the blended polymer-tooth whitening agent composition of step (i).

10. The method of claim 9, wherein a solvent or water is additionally present in the blended polymer-tooth whitening agent composition of step (i).

11. The method of claim 1, further comprising after the extruding step, pressing the extruded teeth whitening composition against a backing member.

12. The method of claim 1, further comprising after the extruding step, laminating the extruded teeth whitening composition to a backing member.

13. The method of claim 3, wherein the thickness of the resulting extruded teeth whitening composition ranges from about 0.050 to 0.80 millimeters.

14. The method of claim 1, wherein the tooth whitening agent mixed in step (i) is in solid form.

15. The method of claim 1, wherein the tooth whitening agent mixed in step (i) is dissolved in a solvent.

16. The method of claim 3, further comprising adding a release liner to the melted composition that has been extruded onto a suitable substrate or backing member.

17. The method of claim 3, wherein the backing member is erodible.

18. The method of claim 2, wherein the tooth whitening agent is a peroxide.

19. The method of claim 5, wherein the extruded tooth whitening composition comprises about 6 weight percent hydrogen peroxide.

20. The method of claim 1, wherein the extruded bioadhesive tooth whitening composition formed in step (iii) is substantially non-tacky but exhibits adhesion upon contact with a moist surface.

21. In a method of preparing a bioadhesive, tooth whitening composition comprising the steps of:
   (i) blending a (1:1) methyacrylic acid-ethyl acrylate copolymer, polyvinylpyrrolidone, and poly(ethylene glycol) having a molecular weight from 200-600, wherein the amount of polyvinylpyrrolidone on a weight basis is greater than the amount of the methyacrylic acid-ethyl acrylate copolymer or the amount of the poly(ethylene)glycol,
   (ii). melting the blended composition from (i) to form a melted composition, and (iii). extruding the melted composition from (ii) to form an, extruded composition, the improvement comprising the inclusion of a tooth whitening agent directly in the blending step to form a blended polymer-tooth whitening agent composition, wherein the extruded tooth whitening composition comprises from about 20-95 wt % polyvinylpyrrolidone, from about 0.5-40 wt % of methyacrylic acid-ethyl acrylate copolymer, and from about 0.5-60 wt % poly(ethylene glycol).

* * * * *